United States Patent
Lemire et al.

(10) Patent No.: US 10,117,798 B2
(45) Date of Patent: Nov. 6, 2018

(54) HOSPITAL BED WITH PATIENT WEIGHT AND DISPLACEMENT SENSORS

(71) Applicant: UMANO MEDICAL INC., L'Islet (CA)

(72) Inventors: Guy Lemire, Beaumont (CA); Richard Labbe, Saint-Vallier (CA); Jimmy Laflamme, Levis (CA); Sylvain Lacasse, Levis (CA); Steve Bolduc, Beaumont (CA); Luc Landry, La Pocatiere (CA); Jean-Philippe Beaudet, L'Islet (CA)

(73) Assignee: UMANO MEDICAL INC., L'Islet (CA)

( * ) Notice: Subject to any disclaimer, the term of this patent is extended or adjusted under 35 U.S.C. 154(b) by 0 days.

(21) Appl. No.: 15/610,592

(22) Filed: May 31, 2017

(65) Prior Publication Data

US 2017/0270772 A1 Sep. 21, 2017

Related U.S. Application Data

(63) Continuation of application No. 14/838,019, filed on Aug. 27, 2015, now Pat. No. 9,754,476.

(Continued)

(51) Int. Cl.
| | |
|---|---|
| *A61G 7/05* | (2006.01) |
| *G08B 21/22* | (2006.01) |
| *A61G 7/00* | (2006.01) |
| *A61B 5/11* | (2006.01) |
| *A61B 5/00* | (2006.01) |
| *G01G 19/02* | (2006.01) |
| *G08B 23/00* | (2006.01) |

(52) U.S. Cl.
CPC .............. *A61G 7/05* (2013.01); *A61B 5/1115* (2013.01); *A61B 5/6891* (2013.01); *A61G 7/00* (2013.01); *A61G 7/0527* (2016.11); *G01G 19/021* (2013.01); *G08B 21/22* (2013.01); *G08B 23/00* (2013.01); *A61G 2203/44* (2013.01)

(58) Field of Classification Search
CPC ........ G08B 21/22; A61G 7/0527; A61G 7/00; A61B 5/1115; A61B 5/6891
USPC ...................................... 340/573.1
See application file for complete search history.

(56) References Cited

U.S. PATENT DOCUMENTS

| | | |
|---|---|---|
| 4,565,910 A | 1/1986 | Musick |
| 4,926,951 A | 5/1990 | Carruth et al. |

(Continued)

*Primary Examiner* — Eric Blount
(74) *Attorney, Agent, or Firm* — Steptoe & Johnson LLP

(57) ABSTRACT

A system for determining a location of a patient on a hospital bed comprising: at least one deformation sensor adapted to generate a signal indicative of a deformation of a frame of the bed; a location determination unit for determining a lateral and/or longitudinal location of the patient based on the deformation of the frame. A method for monitoring an exit of a patient from a hospital bed comprising: determining a patient location on the bed based on measured deformation and generating an alarm signal if the determined location is outside a predetermined area. A weight sensing system for a hospital bed having a base with a suspended frame suspended from a fixed frame comprising: a load sensor connecting the suspended frame and the fixed frame via a suspension member which is unsecured from the fixed frame to allow free vertical movement of the suspended frame relative to the fixed frame.

22 Claims, 22 Drawing Sheets

Related U.S. Application Data

(60) Provisional application No. 62/042,406, filed on Aug. 27, 2014.

(56) References Cited

U.S. PATENT DOCUMENTS

| | | | |
|---|---|---|---|
| 4,974,692 A * | 12/1990 | Carruth | G01G 19/445 177/144 |
| 5,173,977 A | 12/1992 | Carruth et al. | |
| 5,276,432 A | 1/1994 | Travis | |
| 5,393,935 A | 2/1995 | Hasty et al. | |
| 5,780,798 A | 7/1998 | Hall-Jackson | |
| 5,802,640 A | 9/1998 | Ferrand et al. | |
| 5,859,370 A | 1/1999 | Suh et al. | |
| 5,906,016 A | 5/1999 | Ferrand et al. | |
| 5,996,150 A | 12/1999 | Blevins | |
| 6,320,510 B2 | 11/2001 | Menkedick | |
| 6,362,439 B1 * | 3/2002 | Reichow | G01G 19/445 177/144 |
| 6,438,776 B2 | 8/2002 | Ferrand et al. | |
| 6,469,263 B1 | 10/2002 | Johnson | |
| 6,822,571 B2 | 11/2004 | Conway | |
| 6,924,441 B1 | 8/2005 | Mobley et al. | |
| 7,030,764 B2 | 4/2006 | Smith | |
| 7,176,391 B2 | 2/2007 | Metz | |
| 7,253,366 B2 | 8/2007 | Bhai | |
| 7,703,158 B2 | 4/2010 | Wilker, Jr. et al. | |
| 8,123,685 B2 * | 2/2012 | Brauers | A61B 5/103 5/11 |
| 8,821,418 B2 | 9/2014 | Meger | |
| 8,921,717 B2 | 12/2014 | Siegel | |
| 2002/0070867 A1 | 6/2002 | Conway | |
| 2003/0090383 A1 * | 5/2003 | Conway | A61B 5/1115 340/665 |
| 2004/0046668 A1 * | 3/2004 | Smith | A61B 5/1115 340/573.7 |
| 2006/0059814 A1 * | 3/2006 | Metz | A61G 7/012 52/309.8 |
| 2015/0157520 A1 * | 6/2015 | Shiery | G01G 19/445 5/600 |

* cited by examiner

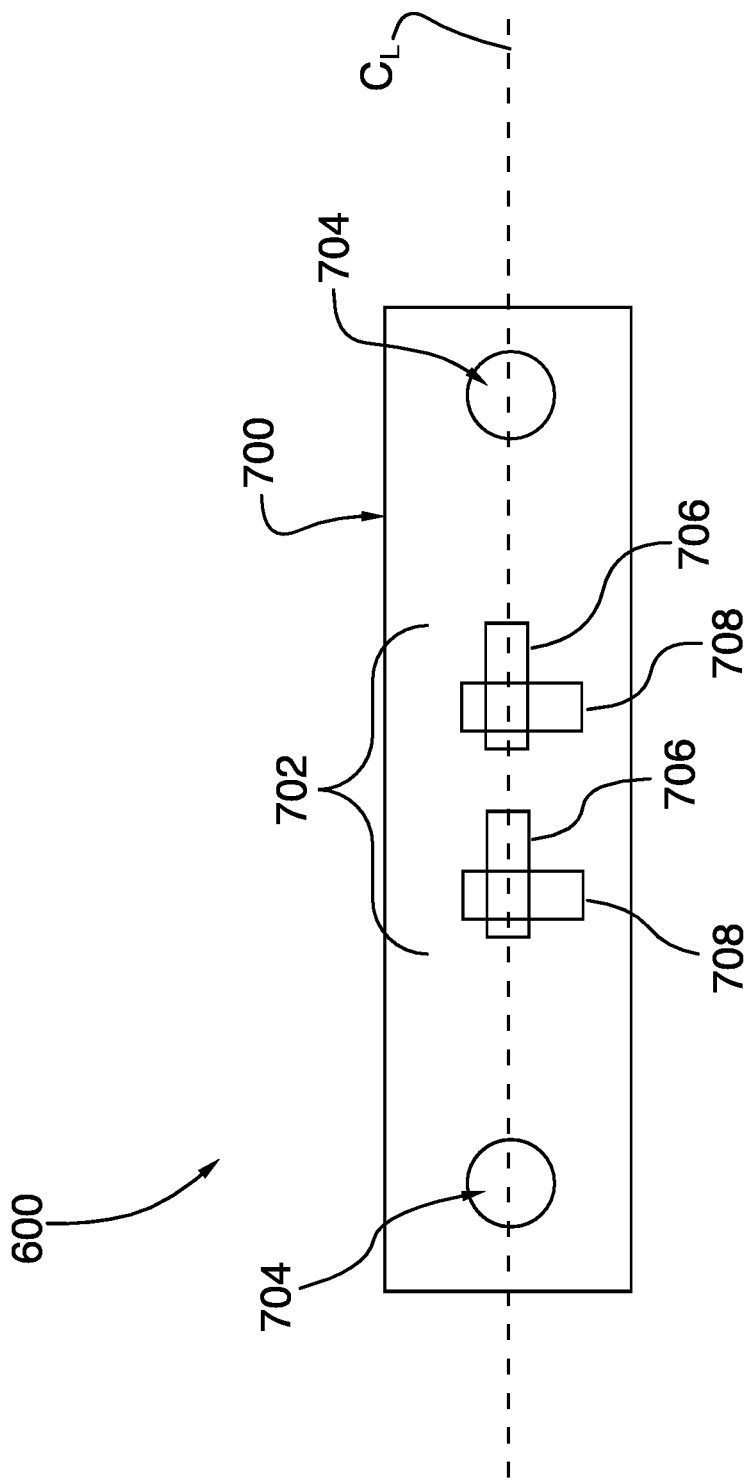

US 10,117,798 B2

HOSPITAL BED WITH PATIENT WEIGHT AND DISPLACEMENT SENSORS

CLAIM FOR PRIORITY

This application is a continuation of U.S. patent application Ser. No. 14/838,019, filed Aug. 27, 2015, which claims priority to U.S. Provisional Patent Application No. 62/042,406, filed Aug. 27, 2014, each of which is incorporated by reference in its entirety.

TECHNICAL FIELD

The present invention relates to patient support apparatuses such as hospital beds. In particular, the invention relates to patient support apparatuses with improved weight and displacement sensors.

BACKGROUND OF THE ART

For various reasons, it may be desirable to determine the weight of the patient lying on a hospital bed. Hospital beds typically comprise a plurality of load cells which are distributed across the area under a sleep surface and are secured to a patient support frame which is provided under the sleep surface.

Some beds comprise three or four load cells which are located generally at the corners or near the perimeter of a sleep surface of the bed. The load cells are generally provided on a patient support frame which is located directly under the sleep surface. The load cells serve two purposes: determining the weight of the patient by calculating a sum of the weight measured by each load cell, and monitoring patient position on the bed by calculating which proportion of the total weight of the patient is measured by each load cell. Examples of this type of bed are shown in U.S. Pat. Nos. 5,276,432 and 5,802,640.

In this type of arrangement, the load cells are configured to measure loads which are applied in a purely vertical direction on them. However, the patient support frame in most hospital beds comprise a plurality of sections which can be angled relative to each other. In this case, the weight of the patient creates a load which is also angled. Additional "compensation" calculations involving trigonometry may therefore be necessary in order to determine vertical components of the load corresponding to the weight of the patient, which can introduce precision errors in the measured weight.

Furthermore, these systems are costly due to the use of at least three load cells. Their installation is also quite complex because they have to account for mechanical hysteresis in the moving parts of the bed which can affect the precision of the weight measurements. Typically, the patient position system requires a lot less precision from the system than the scale system, but since both systems use the same sensors, the implementation of the patient position monitoring system remains costly.

Other beds include external accessories which are surfaces including a large number of load cells which are placed under the mattress or directly under the patient. An example of this type of bed is shown in U.S. Pat. No. 5,393,935. These accessories are frequently damaged and must be replaced periodically. They must also be cleaned periodically, which further increases the cost of this technology.

To accurately measure weight using load cells, it may also be necessary to reduce lateral forces applied on the load cell, which can cause torsion in the load cells and disturb the weight measurements. In order to reduce these lateral forces, some solutions have been proposed, including rigidifying the frame to reduce deflection of the frame caused by bending and placing the load cells relatively close to the patient. However, these solutions can be costly and complex because they involve redesigning a large portion of the frame.

It has been proposed to mount the sleep surface on a movable frame and to movably connect the movable frame to a fixed frame which sits on the ground with the load cells in order to isolate the purely vertical load created by the weight of the patient. US Patent Publication No. 2015/0157520, for example, uses elastic members to connect the two frames together. However, this connection may still transmit some lateral forces to the load cells. Furthermore, a lateral push on the side of the bed may cause undesirable movement of the sleep surface relative to the fixed frame.

Examples of prior art hospital beds are described in U.S. Pat. Nos. 4,926,951, 5,173,977, 5,859,390, 5,906,016, 6,362,439, 5,276,432, 5,393,935, 4,974,692, 6,924,441, 5,802,640, 6,438,776, 7,253,366, 7,703,158 and 8,921,717, and US Patent Publication No. 2015/0157520.

SUMMARY

According to one aspect, there is provided a system for determining a location of a patient on a hospital bed, said hospital bed having a patient support assembly supported on a frame, said system comprising: at least one deformation sensor secured to the frame, said at least one deformation sensor being adapted to generate a signal indicative of a deformation of said frame; a location determination unit operatively connected to said at least one deformation sensor for receiving the signal therefrom and for determining at least one of a lateral and longitudinal location of the patient on the patient support assembly based on said deformation of said frame.

In one embodiment, each one of the at least one deformation sensor is secured to a longitudinal frame member of the frame.

In one embodiment, the system further comprises an output device operatively connected to the location determination unit for generating an alarm signal when the determined location is outside of a predetermined area.

According to another aspect, there is also provided a method for monitoring an exit of a patient from a hospital bed, said hospital bed having a patient support assembly supported on a frame, the method comprising: providing at least one deformation sensor secured on the frame; measuring a deformation of the frame using the at least one deformation sensor; determining a location of the patient on the patient support assembly based on the measured deformation; generating an alarm signal if the determined location is outside a predetermined area.

In one embodiment, determining a location of the patient on the bed comprises receiving from the at least one deformation sensor a signal indicative of a deformation of the frame.

In one embodiment, the signal comprises a voltage value.

In one embodiment, the location of the patient comprises at least one of a transversal location and a longitudinal location.

According to another aspect, there is also provided a weight sensing system for a hospital bed, said hospital bed having a patient support assembly mounted onto a base, said base having a fixed frame and a suspended frame, said fixed frame contacting the ground, said suspended frame supporting said patient support assembly and being suspended from said fixed frame, said weight sensing system comprising: at least one load sensor connecting the suspended frame and the fixed frame, said suspended frame being vertically suspended from said fixed frame via the load sensor; at least one suspension member extending between the fixed frame and one of the at least one load sensor, each suspension member having a lower end secured to one of the at least one load sensor and an upper end abutting the fixed frame, the suspension member being unsecured from the fixed frame to allow free vertical movement of the suspended frame relative to the fixed frame.

In one embodiment, each suspension member comprises a body located near the lower end of the suspension member for engaging the load sensor and a head abutting the fixed frame.

In one embodiment, the suspension member is inserted in a hole of the fixed frame, the hole having a first diameter and the head of the suspension member having a second diameter larger than the first diameter to maintain the head above the fixed frame.

In one embodiment, the head of the suspension member is tapered towards the body of the suspension member and abuts an edge of the hole.

In one embodiment, the head of the suspension member has an upper end having the second diameter and a lower end having a third diameter smaller than the first and second diameters to allow the lower end of the head to extend below the edge of the hole.

In one embodiment, the head of the suspension member is conical.

BRIEF DESCRIPTION OF THE DRAWINGS

Having thus generally described the nature of the invention, reference will now be made to the accompanying drawings, showing by way of illustration example embodiments thereof and in which:

FIG. 7 is a schematic drawing of the deformation sensor shown in FIG. 6B;

DETAILED DESCRIPTION

Figure 1:
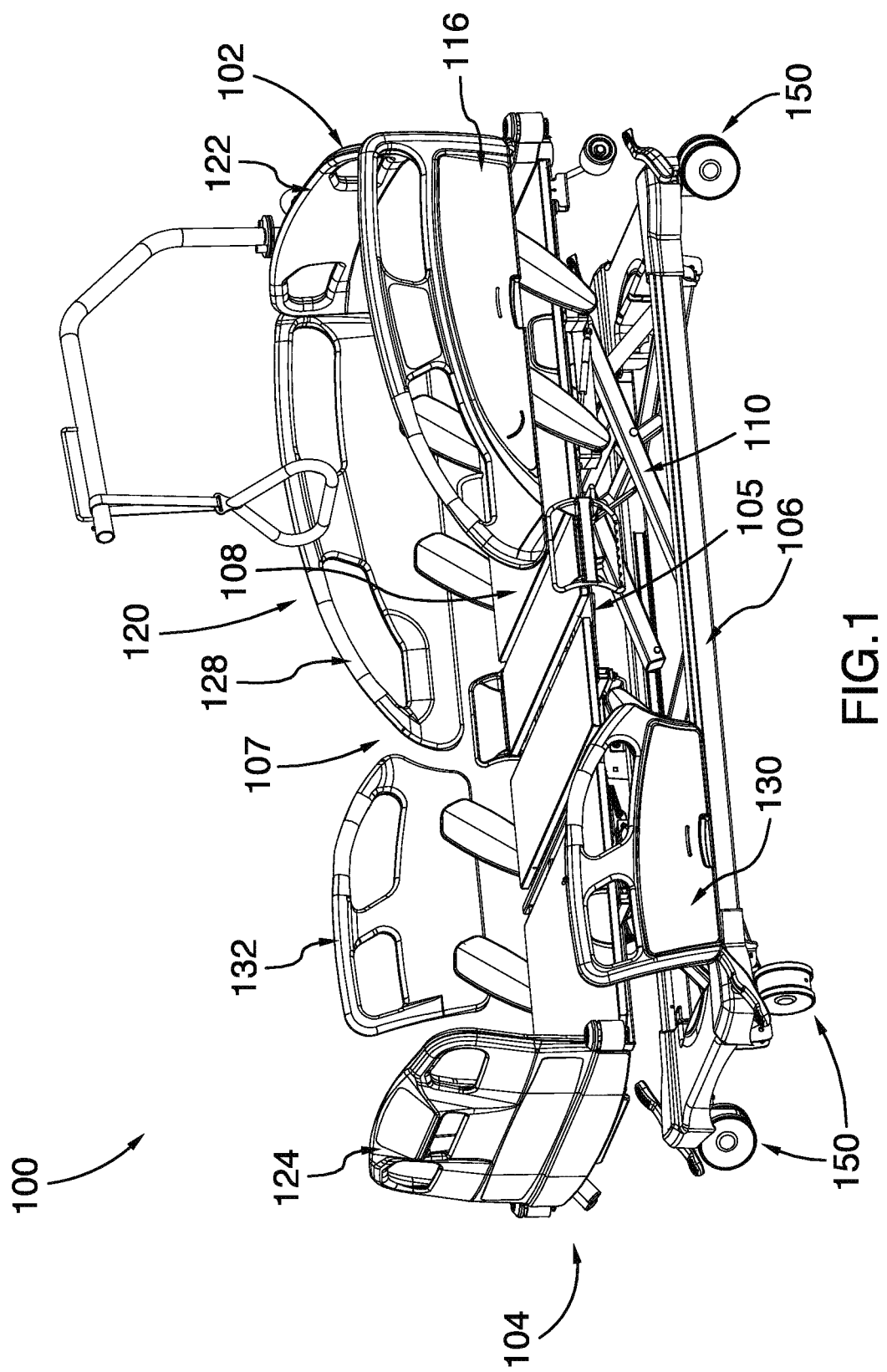
FIG. 1 is a top perspective view of a hospital bed, in accordance with one embodiment, with the elevation system in the lowered position.
Figure 2:
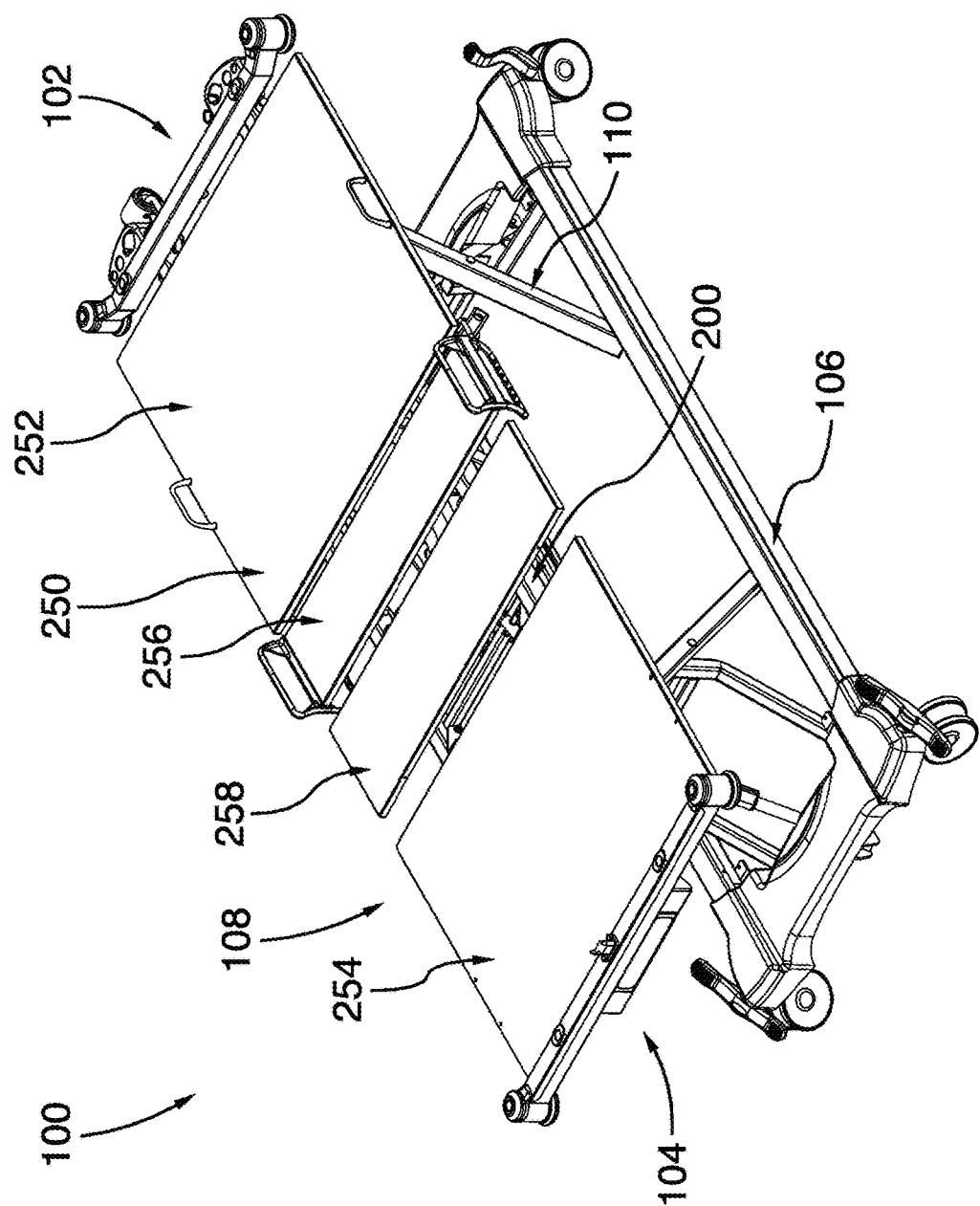
FIG. 2 is a top perspective view of the bed illustrated in FIG. 1, with the siderails removed and with the elevation system in the raised position.

Referring first to FIGS. 1 and 2, there is shown a hospital bed 100, in accordance with one embodiment. The bed 100 comprises a head end 102, an opposite foot end 104 and spaced-apart left 105 and right 107 sides extending between the head end 102 and the foot end 104.

Some of the structural components of the bed 100 will be designated hereinafter as "right", "left", "head" and "foot" from the reference point of an individual lying on his/her back on the support surface of the mattress provided on the bed 100 with his/her head oriented toward the head end 102 of the bed 100 and the his/her feet oriented toward the foot end 104 of the bed 100.

The bed 100 includes a base 106, a patient support assembly 108 and an elevation system 110 operatively coupling the patient support assembly 108 to the base 106. In the illustrated embodiment, the patient support assembly 108 includes a frame 200 (best shown in FIG. 3) and a patient support surface 250 supported by the frame 200. In the illustrated embodiment, the patient support surface 250 includes an upper body surface or backrest 252, a lower body surface or lower body support panel 254 and one or more core body surfaces or core support panels 256, 258 located between the backrest 252 and the lower body support panel 254 for supporting the seat and/or thighs of the patient. In the illustrated embodiment, each one of the backrest 252, the lower body support panel 254 and the core support panels 256, 258 can be angled relative to the other panels. Alternatively, the patient support surface 250 could comprise a single rigid panel extending between the head end 102 and the foot end 104 of the bed 100 instead of multiple pivotable panels.

Referring specifically to FIG. 1, the bed 100 further includes a patient support barrier system 120 generally disposed around the patient support assembly 108. The barrier system 120 includes a plurality of barriers which extend generally vertically around the patient support assembly 108. In the illustrated embodiment, the plurality of barriers includes a headboard 122 located at the head end 102 and a footboard 124 disposed generally parallel to the headboard 122 and located at the foot end 104 of the bed 100. The plurality of barriers further include spaced-apart left and right head siderails 126, 128 which are located adjacent the headboard 122 and spaced-apart left and right foot siderails 130, 132 which are respectively located between the left and right head siderails 126, 128 and the foot end 104 of the bed 100. Each one of the plurality of barriers is moveable between an extended or raised position for preventing the patient lying on the bed 100 from moving laterally out of the bed 100, and a retracted or lowered position for allowing the patient to move or be moved laterally out of the bed 100.

The bed 100 may further include a control interface (not shown) for controlling features of the bed 100. The control interface could be integrated into the footboard 124, into the headboard 122 or into one or more of the siderails 126, 128, 130, 132. Alternatively, the control interface could be provided as a separate unit located near the bed 100 or even at a location remote from the bed 100. In one embodiment, the control interface is operatively connected to the elevation system 110 to control the height of the patient support assembly 108 above the floor.

Figure 3:
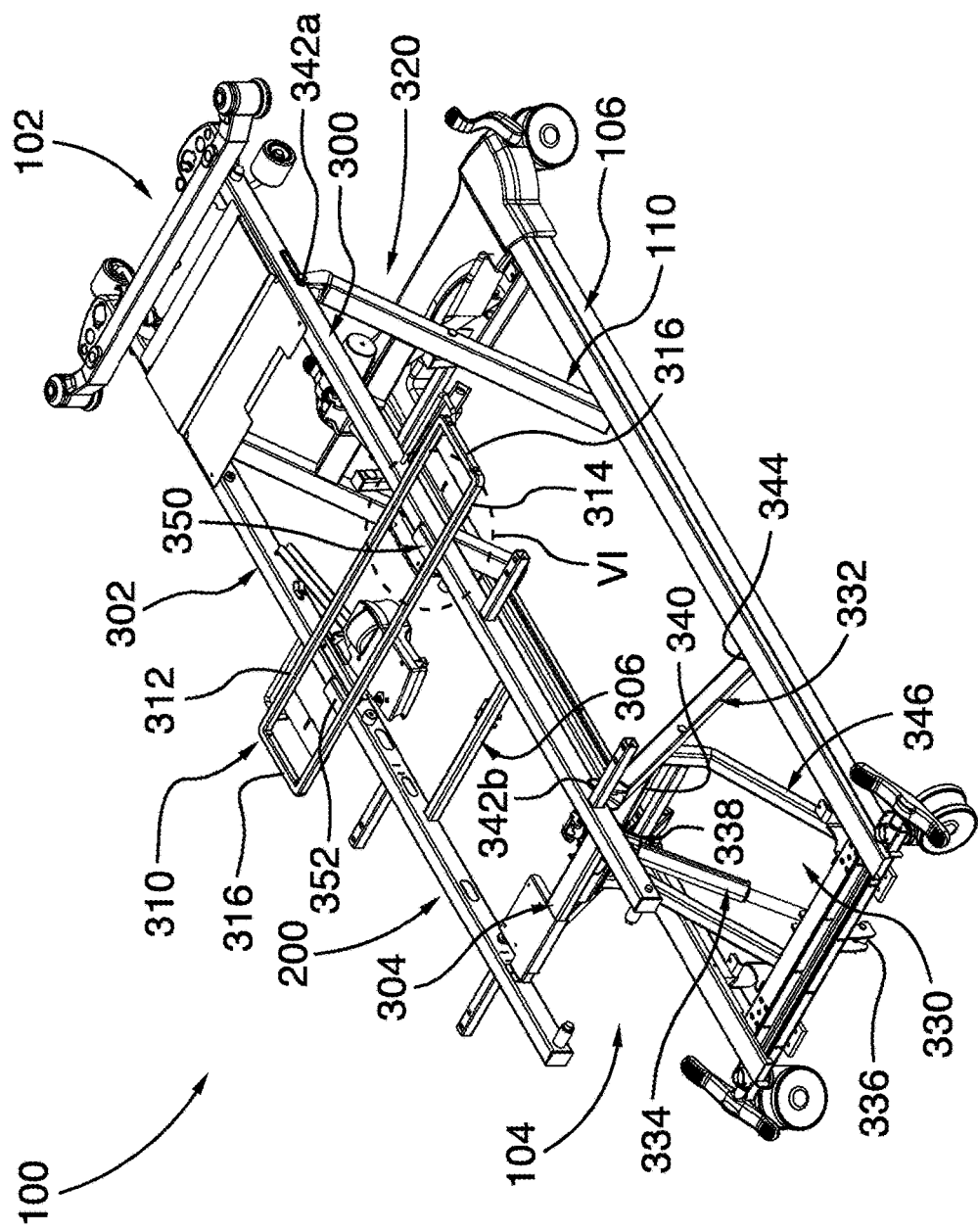
FIG. 3 is a top perspective view of the bed similar to that shown in FIG. 2, with the patient support surface further removed to reveal details of the construction of the bed.
Figure 4:
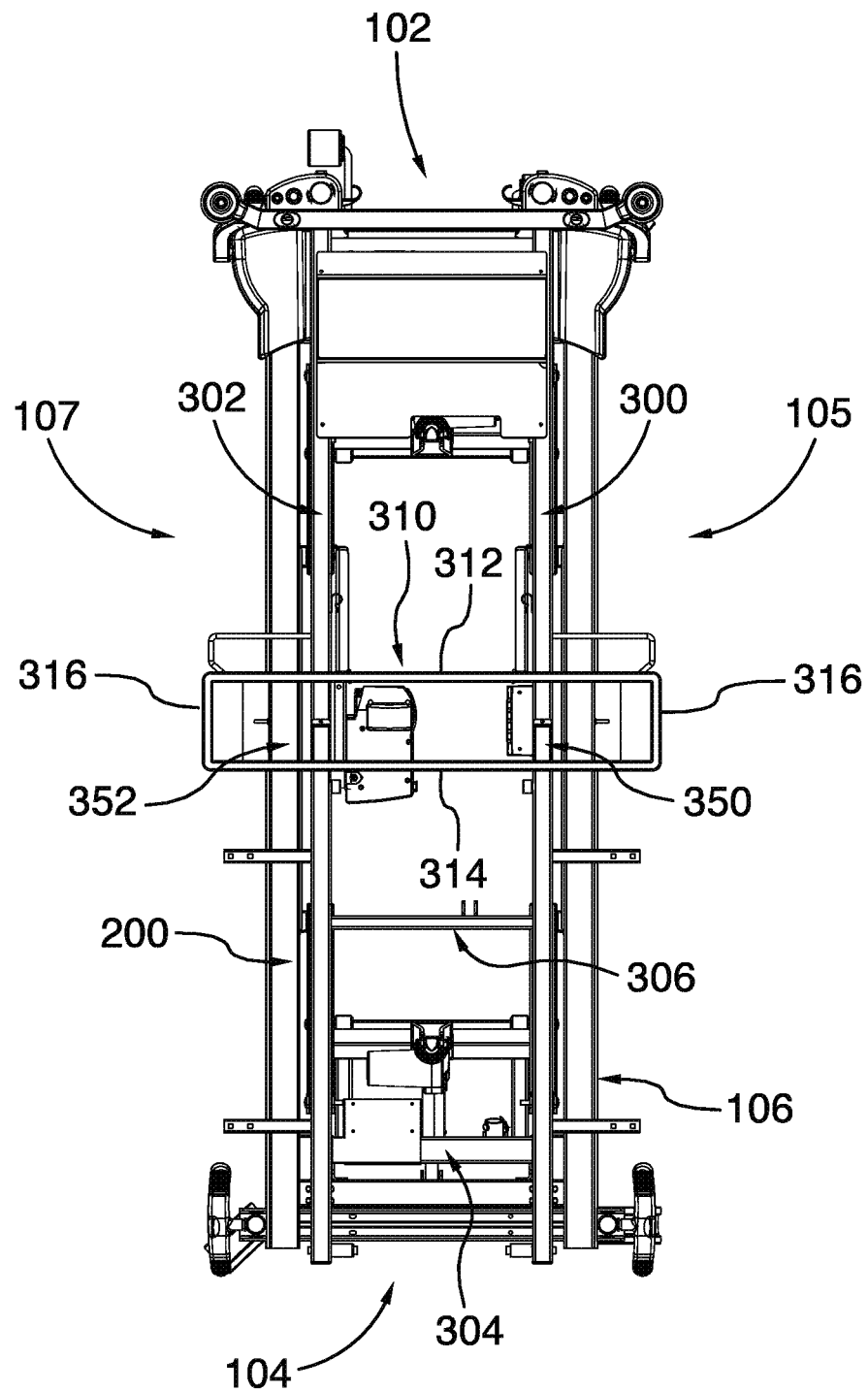
FIG. 4 is a top plan view of the bed illustrated in FIG. 3.
Figure 5:
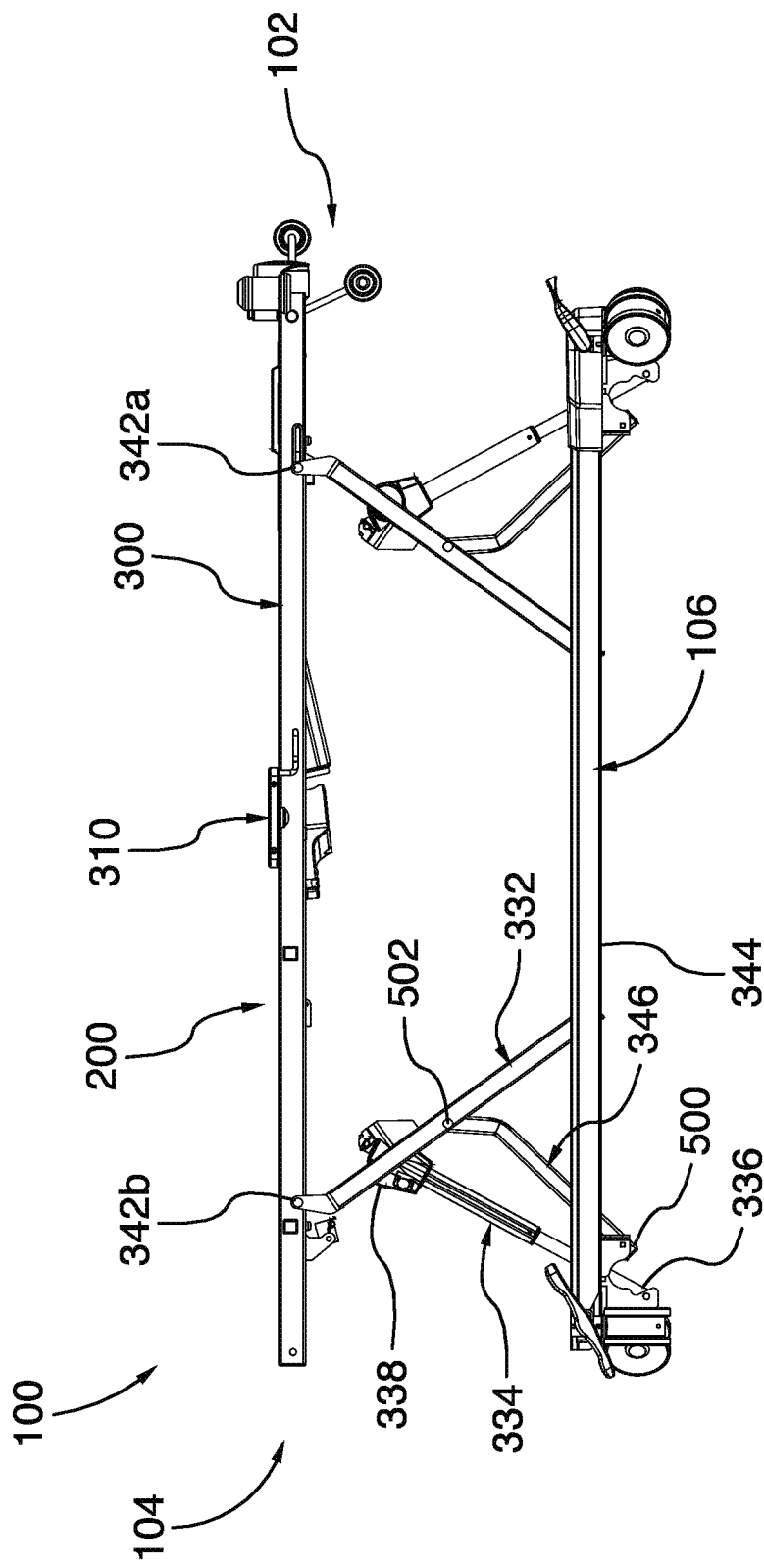
FIG. 5 is a right side elevation view of the bed illustrated in FIG. 3.

Now referring to FIGS. 3, 4 and 5, the frame 200 includes a pair of longitudinal frame members 300, 302 and a plurality of transversal frame members extending between the longitudinal frame members 300, 302. In the illustrated embodiment, the plurality of transversal members include a foot transversal member 304 located near the foot end 104 of the bed 100 and an intermediate transversal member 306 which is disposed between the foot transversal member 304 and the head end 102 of the bed 100. Alternatively, the frame 200 could include additional transversal members, or a single transversal frame member instead of a plurality of transversal members.

Still in the illustrated embodiment, the frame 200 further comprises a core panel frame 310 secured to the left and right longitudinal frame members 300, 302 and secured on top of the longitudinal frame members 300, 302. The core panel frame 310 is adapted for receiving the core support panel 256 adjacent the backrest 252. More specifically, the size and shape of the core panel frame 310 generally correspond to the size and shape of the core support panel 256, and the core support panel 256 can be secured to the core panel frame 310 using fasteners or adhesive, could be welded on the core panel frame 310, or could be secured using any other technique deemed by the skilled addressee to be suitable. In the illustrated embodiment, the core panel frame 310 is generally rectangular and elongated, and comprises parallel head and foot transversal members 312, 314 and a pair of parallel side members 316 which extend between and connect together the head and foot transversal members 312, 314. The core panel frame 310 could be configured differently or, alternatively, the frame 200 may not comprise a core panel frame, the core support 256 panel being instead secured directly to the longitudinal frame members 300, 302.

Still referring to FIGS. 3, 4 and 5, the elevation system 110 is configured to raise and lower the patient support assembly 108 relative to the base 106 between a minimum or fully lowered position and a maximum or fully raised position. In one embodiment, the elevation system 110 is further configured to allow the patient support assembly 108 to be set at any intermediate position between the fully lowered and fully raised positions. The elevation system 110 may further be configured to tilt the patient support assembly 108 in various orientations.

More specifically, the elevation system 110 comprises a head elevation assembly 320 located near the head end 102 of the bed 100 and a foot elevation assembly 330 located near the foot end 104 of the bed 100. In the illustrated embodiment, the head and foot elevation assemblies 320, 330 are similar to each other. Specifically, the head and foot elevation assemblies 320, 330 are mirror images of each other. Therefore, only the foot elevation assembly 330 will be described, with the same description applying to the head elevation assembly 320.

The foot elevation assembly 330 comprises a pair of pivoting leg members 332 and an elevation actuator 334 connecting the base 106 to the pivoting leg members 332. Specifically, the elevation actuator 334 has a lower end 336 pivotably connected to the base 106 and an upper end 338 pivotably connected to a transverse elevation member 340 extending between the pivoting leg members 332. Each pivoting leg member 332 comprises an upper leg end 342a, 342b pivotably connected to a respective one of the left and right longitudinal frame members 300, 302 and a lower leg end 344 pivotably and movably connected to the base 106. Specifically, the head elevation assembly 320 includes an upper leg end 342a and the foot elevation assembly 330 includes an upper leg end 342b.

Still in the illustrated embodiment, the foot elevation assembly 330 further comprises left and right pivoting links 346 pivotably connecting the base 106 to the left and right pivoting leg members 332. Each pivoting link 346 has a generally dogleg shape (generally resembling the shape of a hockey stick) and has a lower end 500 pivotably connected to the base 106 and an upper end 502 pivotably connected to a respective pivoting leg member 332, as best shown in FIG. 5.

Referring specifically to FIGS. 3 and 4, the bed 100 further comprises at least one deformation sensor adapted to determine a deformation of the frame 200, which can be used to determine a location of the patient on the bed 100 in order to help medical personnel monitor a patient lying on the bed, as will be further explained below. More specifically, the bed 100 comprises a left deformation sensor assembly 350 operatively connected to the left longitudinal frame member 300 and a right deformation sensor assembly 352 operatively connected to the right longitudinal frame member 302. Both the left and right deformation sensor assemblies 350, 352 are generally located at the same location longitudinally relative to the bed 100. In the illustrated embodiment, both the left and right deformation sensor assemblies 350, 352 are generally located halfway between the head end 102 and the foot end 104 of the bed 100, as best shown in FIG. 4.

Figure 6:
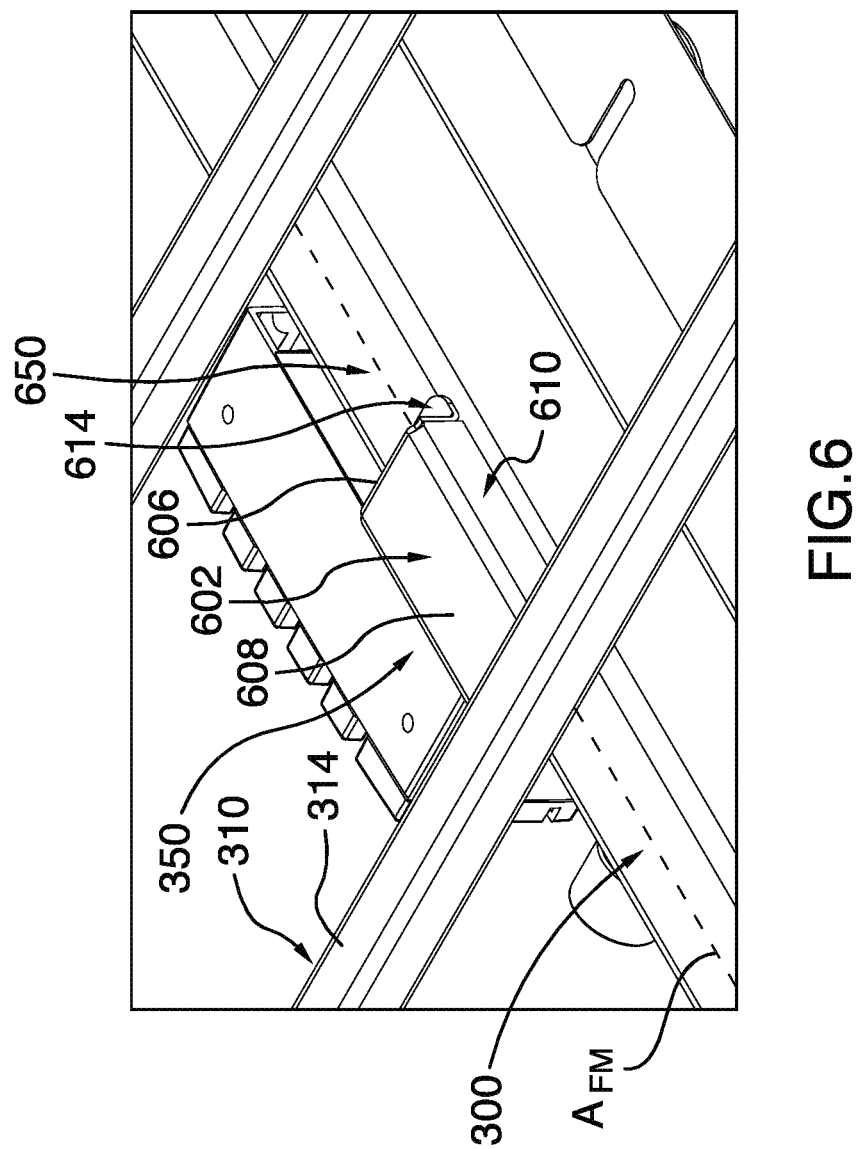
FIG. 6 is a partial top front perspective view of the bed illustrated in FIG. 3 taken from the encircled area VI, enlarged to show details of the deformation sensor assembly.
Figure 6A:
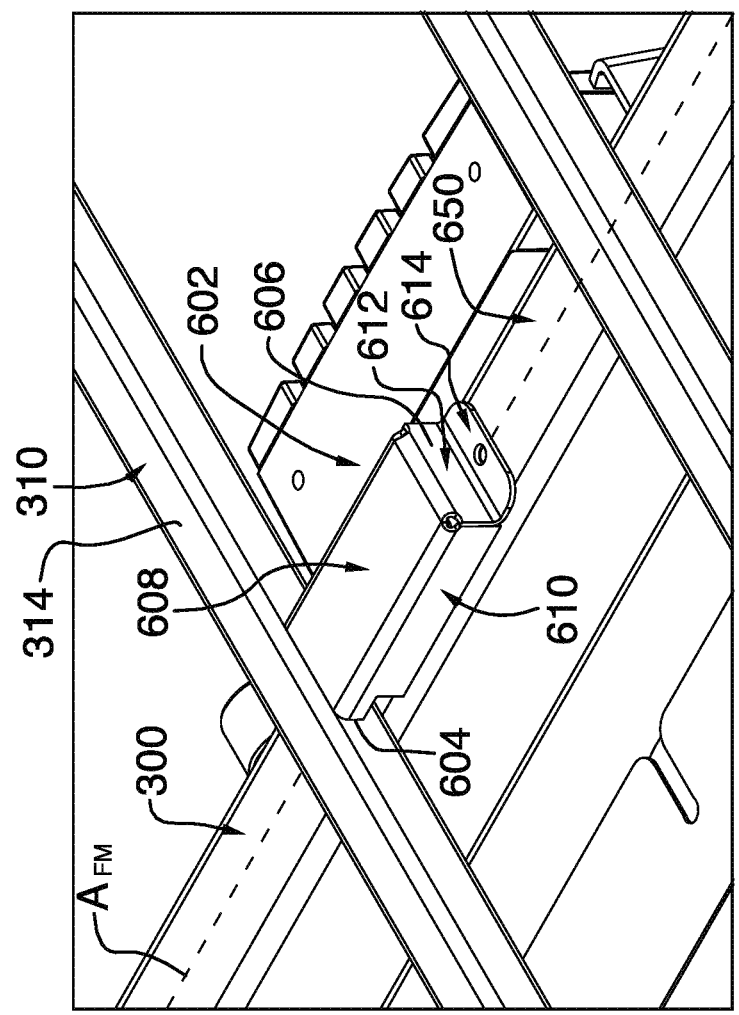
FIG. 6A is a partial top rear perspective view of the bed illustrated in FIG. 3 taken from the encircled area VI, enlarged to show details of the deformation sensor assembly.
Figure 6B:
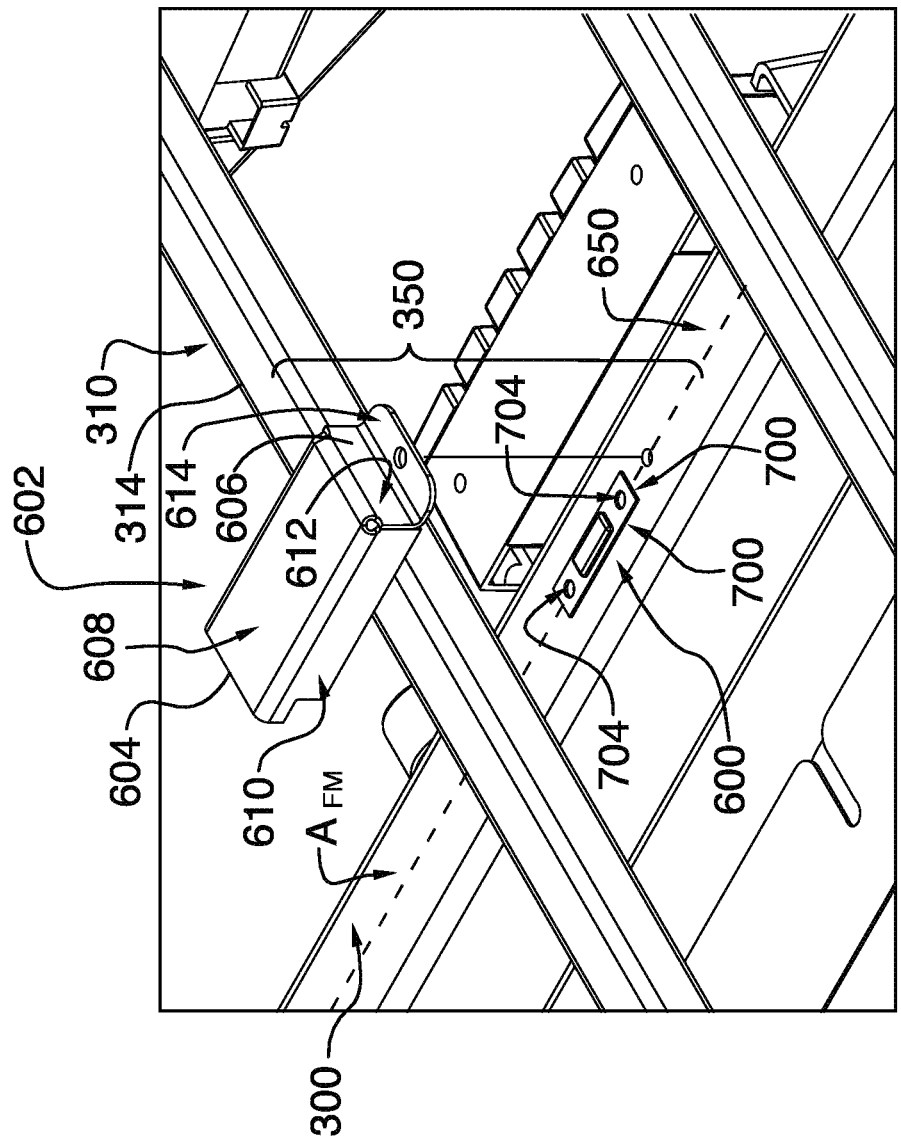
FIG. 6B is a partial top rear perspective view of the bed similar to that shown in FIG. 6A, but with the casing exploded from the frame.

As shown in FIGS. 6 to 6B, each deformation sensor assembly 350, 352 comprises a deformation sensor 600 secured to an upper planar surface 650 of the corresponding longitudinal frame member 300, 302 and a casing 602 covering the deformation sensor 600 to protect the deformation sensor.

Referring specifically to FIG. 7, the deformation sensor 600 comprises a generally rectangular mounting plate 700 and a plurality of strain gauges 702 mounted on the mounting plate 700. The mounting plate 700 is elongated and is disposed such that its longitudinal centerline $C_L$ is generally parallel to a longitudinal axis $A_{FM}$ of the longitudinal frame member 300. The mounting plate 700 further has two mounting holes 704 located along the longitudinal centerline and adapted to receive fasteners (not shown) to secure the mounting plate 700 on the upper surface 650 of the longitudinal frame member 300 such that the mounting plate 700 is deformed similarly to the upper surface 650 of the longitudinal frame member 300. It will be appreciated that when a downward force is applied onto the longitudinal frame member 300, its upper surface 650 is compressed longitudinally and therefore, the mounting plate 700 and the strain gauges 702 mounted thereon are also compressed longitudinally.

Alternatively, the deformation sensor 600 could be secured to the underside of the longitudinal frame member 300. It will be appreciated that when a downward force is applied onto the longitudinal frame member 300, its underside is placed in tension (i.e. stretched longitudinally) and therefore, the mounting plate 700 and the strain gauges 702 mounted on the mounting plate would also be stretched longitudinally in this embodiment. In another embodiment, the deformation sensor 600 could be configured to be mounted to a lateral surface of the longitudinal frame member 300 or to any other suitable surface of the longitudinal frame member 300.

In the illustrated embodiment, the deformation sensor 600 comprises four strain gauges 702, including two strain gauges 706 mounted parallel to the longitudinal centerline $C_L$ of the mounting plate 700 and two strain gauges 708 mounted perpendicular to the longitudinal centerline $C_L$. In one embodiment, all four strain gauges 706, 708 are connected together in a Wheatstone bridge in a full or complete bridge configuration. It will be appreciated that this configuration provides a relatively high sensitivity to measure relatively small deformations of the longitudinal frame members 300, 302. Alternatively, the deformation sensor 600 may comprise only two strain gauges mounted parallel to the longitudinal centerline $C_L$ of the mounting plate 700 and connected together in a Wheatstone bridge in a half-bridge configuration. In another embodiment, the deformation sensor 600 may instead comprise a single strain gauge mounted parallel to the longitudinal centerline $C_L$ of the mounting plate 700 and mounted in a Wheatstone bridge in a quarter-bridge configuration. The single strain gauge could also be used without a Wheatstone bridge configuration.

In one embodiment, the strain gauges 702 are glued on the mounting plate. Alternatively, the strain gauges 702 could be secured using any other securing techniques known to the skilled addressee.

Referring back to FIGS. 6 to 6B, the casing 602 is generally rectangular and elongated, and has a foot end 604 located towards the foot end 104 of the bed 100 and an opposed head end 606 located towards the head end 102 of the bed 100. The casing 602 comprises a generally horizontal top wall 608, a pair of generally vertical lateral walls 610 and a head end wall 612 located towards the head end 102 of the bed 100. The casing 602 is disposed such that the top wall 608 extends generally parallel to and opposite the planar upper surface 650 of the longitudinal frame member 300 such that the lateral walls 610 extend between and connect together the top wall 608 and the planar upper surface 650. In the illustrated embodiment, the casing 602 is further disposed such that its foot end 604 abuts the foot transversal member 314 of the core panel frame 310, which closes off the foot end 604 of the casing 602. The deformation sensor 600 is therefore located between the top wall 608 and the planar upper surface 650 of the longitudinal frame member 300, and between the lateral walls 610 of the casing 602. In this configuration, the casing 602 and the longitudinal frame member 300 together encase and protect the deformation sensor 600 on all sides.

The casing 602 further comprises a generally rectangular mounting flange 614 extending away from the head end 606 for mounting the casing 602 to the upper surface 650 of the corresponding longitudinal frame member 300. The flange 614 is disposed against the planar surface 650 and is fastened to the longitudinal frame member 300 using a fastener (not shown) which is inserted through the flange 614 and into the longitudinal frame member 300. In one embodiment, the fastener is a removable fastener such as a screw to allow the casing 602 to be easily removed, for example to perform maintenance on the deformation sensor 600. It will be appreciated that in this configuration, the casing 602 is secured to the longitudinal frame member 300 at a single attachment point (i.e. the flange) instead of the lateral walls 610 being secured to the longitudinal frame member 300 along their entire length. This prevents the casing 602 from stiffening the longitudinal frame member 300 locally near the deformation sensor 600, which may reduce deformations measured by the deformation sensor 600. Alternatively, the lateral walls 610 of the casing 602 may be secured to the longitudinal frame member 300 along their entire length by welding, gluing or any other attachment technique deemed by the skilled addressee to be suitable.

In the illustrated embodiment, the deformation sensor assemblies 350, 352 are located about halfway between the upper leg end 342a of the head elevation assembly 320 and the upper leg end 342b of the foot elevation assembly 330, as best shown in FIGS. 3 and 4. It will be understood that the deformation sensors 600 are placed at locations where the longitudinal frame members 300, 302 are likely to be deformed by a relatively large amount, in order to obtain a relatively clear and accurate signal of the deformation from the deformation sensors 600. In another embodiment in which the frame 200 and the patient support surface 250 have a different configuration, the deformation sensors 600 could be located at another location along the longitudinal frame members 300, 302.

In one embodiment, the deformation sensors 600 may be connected to a location determination unit 800 (shown in FIG. 8) via wires. In the illustrated embodiment, the casing 602 further has two openings 616 located in the lateral walls 610 at the foot end 604 of the casing 602 to allow wires (not shown) connected to the deformation sensor 600 to pass therethrough. Alternatively, the casing 602 could have only a single opening on one of the lateral walls 610. In another embodiment, the casing 602 may not comprise any opening, and the deformation sensor 600 could be connected wirelessly to the location determination unit 800.

Figure 8:
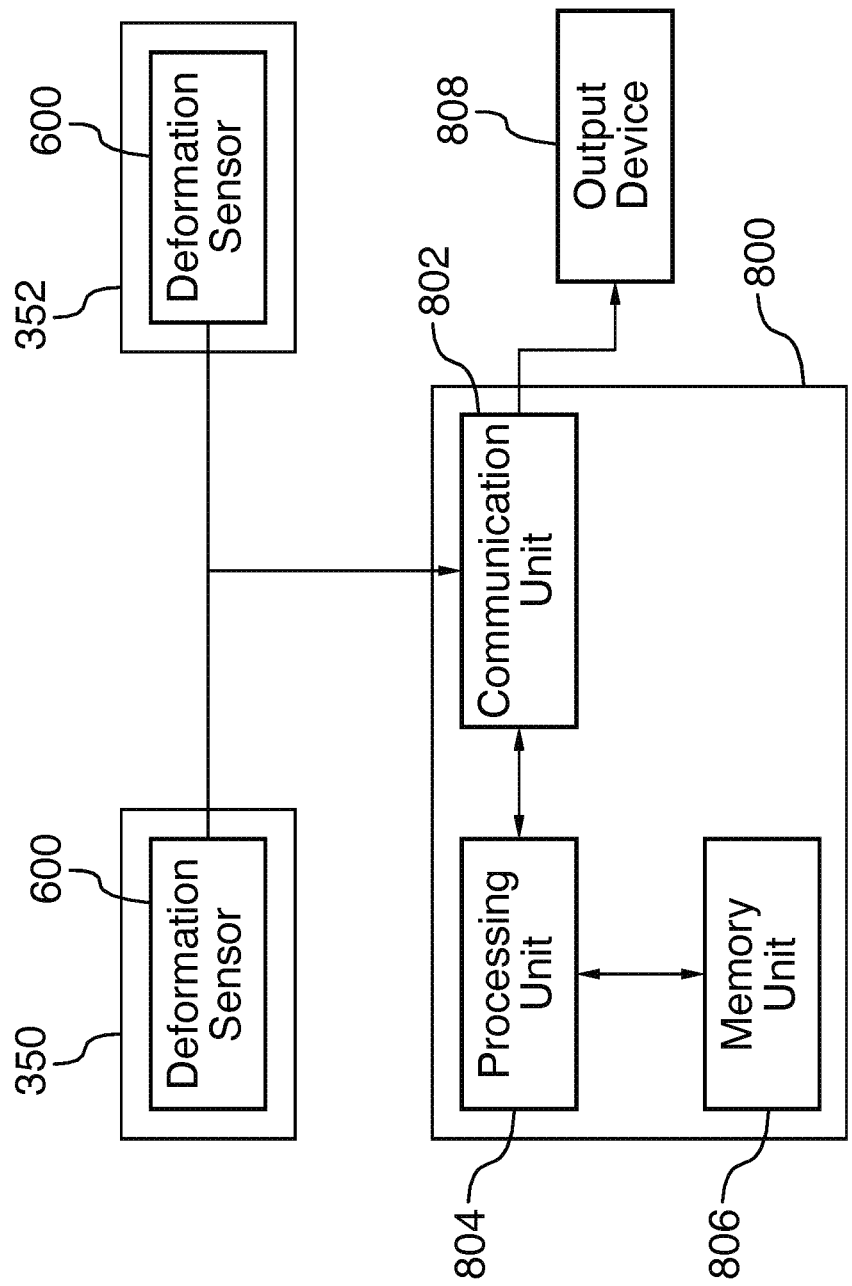
FIG. 8 is a diagram of a system for determining the location of a user on the bed shown in FIG. 1 based on a deformation of the frame.

Referring now to FIG. 8, the location determination unit 800 is configured for determining a location of the patient based on the signal received from the deformation sensors 600. In the illustrated embodiment, the location determination unit 800 includes a communication unit 802 operatively connected to the deformation sensors 600 of the left and right deformation assemblies 350, 352 to receive from the deformation sensors 600 a signal indicative of a deformation of the longitudinal frame member 300, 302 on which the deformation sensor 600 is secured. The location determination unit 800 further comprises a processing unit 804 operatively connected to the communication unit 802 for determining a location of the patient based on the signal received from the deformation sensors 600, as will be further explained below. The location determination unit 800 further comprises a memory unit 806 operatively connected to the processing unit 804 for storing one or more value which can be compared to the signal received, as will also be explained below. In the illustrated embodiment, the communication unit 802 is further operatively connected to an output device 808 for generating an alarm signal in response to one or more selected conditions.

In one embodiment, the location determination unit 800 comprises the control interface of the bed 100. Alternatively, the deformation sensors 600 may be connected to another unit which is distinct from the control interface.

Figure 8A:
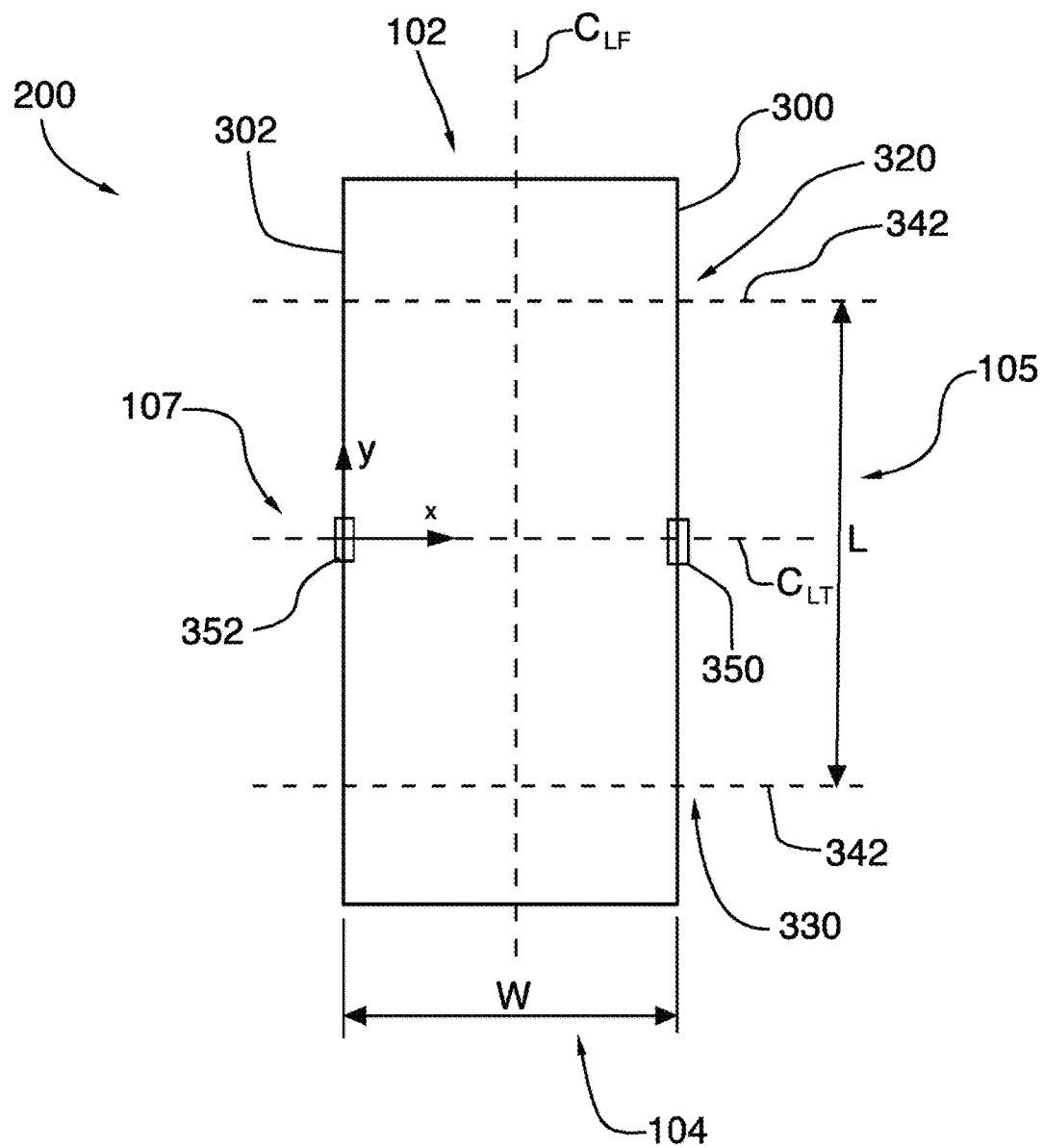
FIG. 8A is a schematic drawing of the frame of the bed shown in FIG. 1, for illustrating the determination of a transversal and/or longitudinal location on the frame using the deformation sensors.
Figure 8B:
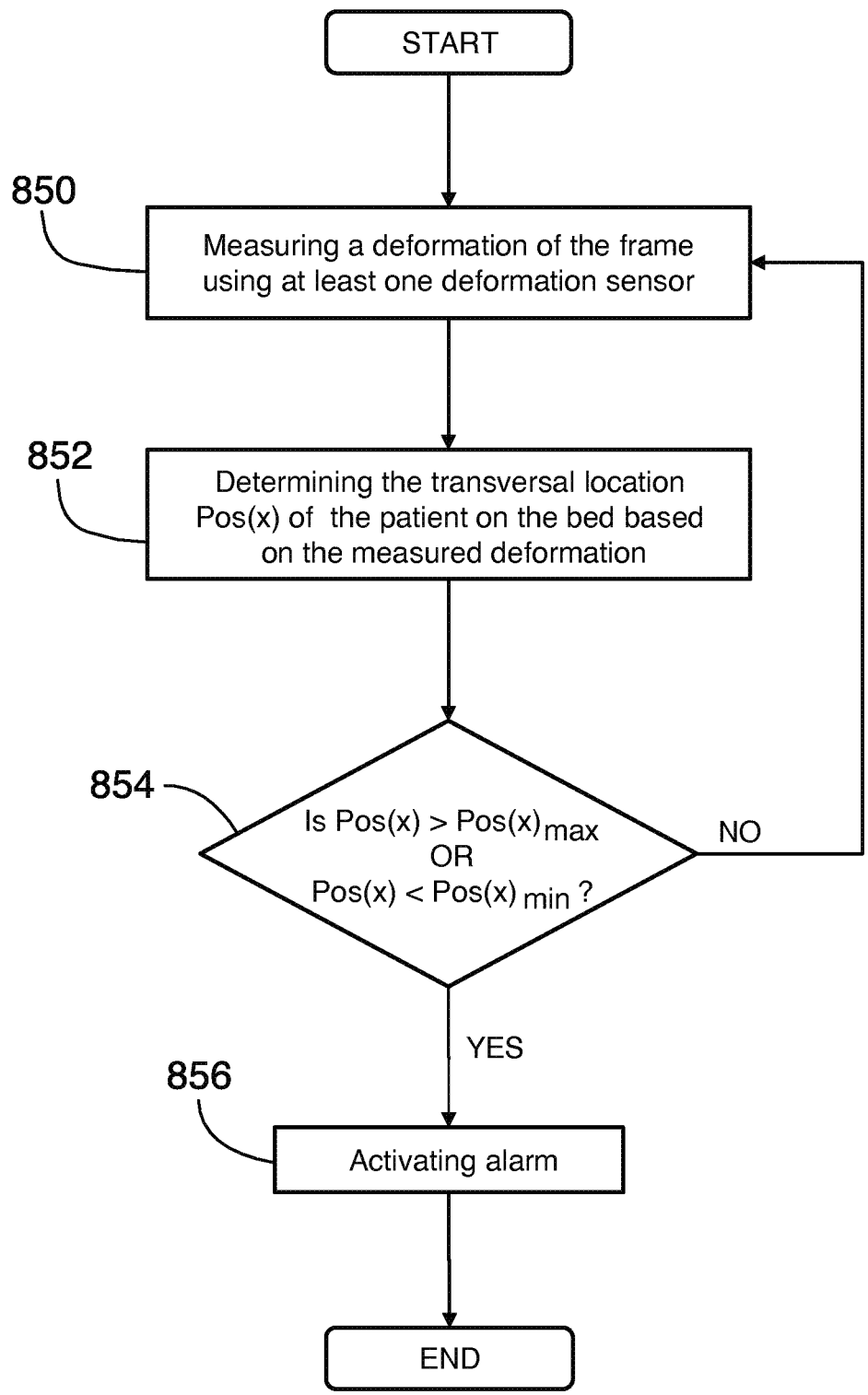
FIG. 8B is a flowchart of a method for determining the location of a user on the bed shown in FIG. 1 based on a deformation of the frame.

Now turning to FIGS. 8A and 8B, a method for determining the transversal location of a patient based on a deformation of the frame will now be described in accordance with one embodiment.

In the illustrated embodiment, the left and right longitudinal members 300, 302 of the frame 200 are spaced apart from each other by a transversal distance W. In one embodiment, the transversal distance W is about 36 inches or 91.4 cm. Alternatively, the transversal distance W could be different.

When the patient is lying on the bed 100, specifically on a mattress placed on the patient receiving surface, the weight of the patient causes the longitudinal frame members 300, 302 to deflect downwardly. In the illustrated embodiment, the entire patient is modeled as a single load application point corresponding to the center of mass of the patient. A change in the transversal location of this load application point indicates a transversal displacement of the patient on the bed 100.

According to 850, a deformation of the frame is measured using the deformation sensors 600. Specifically, the location determination unit 800 receives from each deformation sensor 600 a signal indicative of a level of deformation of the longitudinal frame member 300, 302 on which the deformation sensor 600 is secured. In the illustrated embodiment, the signal comprises a voltage value, which varies as the longitudinal frame members 300, 302 are deformed. The ratio between the voltage value VG of the left deformation sensor assembly 350 and the voltage value VD of the right deformation sensor assembly 352 is proportional to the transversal distance of the load application point from a longitudinal centerline $C_{LF}$ of the frame 200. Therefore, the voltage values VG and VD being equal indicates that the load application point is on the longitudinal centerline $C_{LF}$ of the frame 200. When the load application point is moved towards one of the left and right longitudinal members 300, 302 by a certain displacement distance, the voltage value changes proportionally in the deformation sensors 600 of both of the deformation sensor assemblies 350, 352. This change in voltage value may be referred to as "impedance change" or "voltage feedback". Specifically, the voltage value transmitted by one of the deformation sensors 600 will be raised proportionally to the displacement distance and the voltage value transmitted by the other one of the deformation sensors 600 will decrease proportionally to the displacement distance, such that the sum of the voltage values VG, VD remains constant.

In one embodiment, the voltage value is higher for the deformation sensor 600 closer to the load application point than the voltage value of the other deformation sensor 600. For example, if the load application point is closer to the left deformation sensor assembly 350, the voltage value VG of the deformation sensor 600 of the left deformation sensor assembly 350 will be higher than the voltage value VD of the deformation sensor 600 of the right deformation sensor assembly 352. Alternatively, the voltage value may be lower for the deformation sensor 600 closer to the load application point than the voltage value of the other deformation sensor 600.

According to 852, the transversal location of the patient on the bed 100, modeled by the load application point, is then determined based on the voltage values VG, VD of the deformation sensors 600, which are indicative of the measured deformation. In the illustrated embodiment, the transversal location of the load application point on the frame 200 is measured from the right longitudinal frame member 302 towards the left longitudinal frame member 300. Specifically, the transversal location of the load application point is measured along an X-axis which has an origin located on the right longitudinal frame member, as shown in FIG. 8A. The transversal location of the load application point can be calculated using the following formula:

$$Pos(x) = W * \frac{VG}{VR + VG} \quad (1)$$

in which Pos(x) corresponds to the transversal location of the load application point, W corresponds to the distance between the left longitudinal member and the right longitudinal member, VG corresponds to the voltage value of the deformation sensor 600 of the left deformation sensor assembly 350, and VR corresponds to the voltage value of the deformation sensor 600 of the right deformation sensor assembly 352.

Alternatively, the transversal location of the load application point can be calculated using the following formula:

$$Pos(x) = W - \left(W * \frac{VR}{VR + VG}\right) \quad (2)$$

From the two formulas (1) and (2) above, it will be understood that a location Pos(x) of 0 corresponds to the load application point being located on the right longitudinal frame member 302. In this case, no deformation is measured in the left longitudinal frame member 300 by the deformation sensor 600 of the left deformation sensor assembly 350, and a maximum deformation is measured in the right longitudinal frame member 302 by the deformation sensor 600 of the right deformation sensor assembly 352.

It will also be understood that a location Pos(x) of W corresponds to the load application point being located on the left longitudinal frame member 300. In this case, no deformation is measured in the right longitudinal frame member 302 by the deformation sensor 600 of the right deformation sensor assembly 352, and a maximum deformation is measured in the left longitudinal frame member 300 by the deformation sensor 600 of the left deformation sensor assembly 350.

In one embodiment, if a load of more than 200 lb is applied at the load application point, the change in voltage value may not be proportional to the transversal displacement distance of the load application point anymore, because the weight of the patient may not be modeled by a single load application point. More specifically, the voltage value of one of the deformation sensors 600 may be raised by a first value, and the voltage value of the other one of the deformation sensors may decrease by a second value which is different from the first value. In this embodiment, the transversal location Pos(x) can be determined with substantial accuracy by calculating an average of a first transversal location value determined using the voltage value VG of the left deformation sensor assembly 350 and a second transversal location value determined using the voltage value VR of the right deformation sensor assembly 352. Specifically, the transversal location Pos(x) of the load application point can be calculated using the following formula:

$$Pos(x) = \frac{1}{2} W * \left(1 + \frac{VG - VR}{VG + VR}\right) \qquad (3)$$

The transversal position of the load application point, and therefore of the patient, on the bed 100, can be monitored in order to detect the patient moving to one or more predetermined location on the bed 100. In one embodiment, a bed exit alarm is activated when the transversal position of the load application point is displaced within a predetermined range of the longitudinal frame members 300, 302, and therefore of the sides 105, 107 of the bed 100. The bed exit alarm could first require the bed 100 to be set in a bed exit alarm mode, through the control interface for example. The bed exit alarm could also be programmed such that a patient may be able to climb into the bed 100 on his own but may need to be supervised when exiting the bed 100. Entry of the patient on the bed 100 could be detected by the deformation sensors 600. A timer can be preset by a user through the control interface to determine an appropriate time for the patient to climb, settle in and stabilize his position in the bed 100. After that elapsed time, if the deformation sensors detect a substantial displacement of the weight of the patient toward one side 105, 107 of the bed 100, the alarm can be triggered.

In the illustrated embodiment, the bed exit alarm comprises an alarm signal generated by the output device 808. The alarm signal could be an audible signal, a visual signal such as a light being turned on or a light flashing, an indicator on a display, or any other type of signal known to the skilled addressee.

In one embodiment, the location determination unit 800 first determines a transversal location of the patient on the bed 100. More specifically, the location determination unit 800 determines the transversal location Pos(x) using an appropriate one of formula (1), (2) and (3) above.

According to 854, the transversal location Pos(x) is then compared to a predetermined minimum threshold value $Pos(x)_{min}$ and a predetermined maximum threshold value $Pos(x)_{max}$.

According to 856, if the transversal location Pos(x) is lower than the predetermined minimum threshold value $Pos(x)_{min}$, then the bed exit alarm is activated. Similarly, if the transversal location Pos(x) is higher than the predetermined maximum threshold value $Pos(x)_{max}$, then the bed exit alarm is activated as well. When the bed 100 is in the bed exit alarm mode, the location determination unit 800 may continuously monitor the transversal location of the patient on the bed 100 and compare this location to the minimum and maximum threshold values $Pos(x)_{min}$, $Pos(x)_{max}$. Alternatively, the transversal location could only be compared to the minimum and maximum threshold values $Pos(x)_{min}$, $Pos(x)_{max}$ when displacement is detected on the bed 100 by the deformation sensors 600.

The control interface may be used to allow the user to set the minimum and maximum threshold values $Pos(x)_{min}$, $Pos(x)_{max}$ in accordance with a desired condition in which the bed exit alarm is to be activated.

In one configuration, the minimum threshold value $Pos(x)_{min}$ is 4 inches or 10.2 cm and the maximum threshold value $Pos(x)_{max}$ is (W−4 inches) or (W−10.2 cm). In an embodiment in which the distance W between the left and right longitudinal members is 36 inches or 91.4 cm, the maximum threshold value $Pos(x)_{max}$ is therefore 32 inches or 81.3 cm. In this configuration, the bed exit alarm is activated when the load application point is displaced within 4 inches or 10.2 cm of the left or right longitudinal frame members 300, 302, which corresponds to the patient most likely having the intention of exiting the bed 100.

In another configuration, the minimum threshold value $Pos(x)_{min}$ is ((W/2)−1 inch) or ((W/2)−2.5 cm) and the maximum threshold value $Pos(x)_{max}$ is ((W/2)+1 inch) or ((W/2+2.5 cm). In an embodiment in which the distance W between the left and right longitudinal members is 36 inches or 91.4 cm, the minimum threshold value $Pos(x)_{min}$ is therefore 17 inches or 43.2 cm and the maximum threshold value $Pos(x)_{max}$ is 19 inches or 48.3 cm. In this configuration, the bed exit alarm is activated when the load application point is displaced within 1 inch or 2.5 cm from the longitudinal centerline $C_{LF}$ of the frame 200, which corresponds to the patient having just woken up and stirring in the bed 100.

In yet another configuration, the minimum threshold value $Pos(x)_{min}$ is 0 and the maximum threshold value $Pos(x)_{max}$ is W (i.e. the distance between the left and right longitudinal members 300, 302). In an embodiment in which the distance W between the left and right longitudinal members 300, 302 is 36 inches or 91.4 cm, the maximum threshold value $Pos(x)_{max}$ is therefore 36 inches or 91.4 cm. It will be appreciated that in this configuration, at least one of the voltage values VG, VR is a negative value, corresponding to a case where at least one of the longitudinal frame members 300, 302 is deflected upwardly or laterally. This may also correspond to a case where at least one of the deformation sensors 600 is malfunctioning.

In one embodiment, the location determination unit 800 could be configured to measure a rate of variation of the transversal location of the load application point as a function of time, to thereby determine a transversal displacement speed of the load application point. In this embodiment, a displacement speed alarm could be activated if the determined displacement speed exceeds a predetermined maximum speed threshold. In another embodiment, a weight change alarm may further be activated in response to a change in the sum of the voltage value VG from the deformation sensor 600 of the left deformation sensor assembly 350 and of the voltage value VR from the deformation sensor 600 of the right deformation sensor assembly 352, which corresponds to weight being added to or removed from the bed 100.

In one embodiment, a patient may be able to enter and exit the bed 100 without supervision but the patient may only be allowed to leave the bed 100 for a predetermined duration (e.g. to go to the bathroom). The exit of the patient is detected by the deformation sensors 600 and a timer is started when the patient exits the bed 100. If the deformation sensors 600 detect that the patient re-enters the bed 100 within the predetermined duration, no alarm is activated and the timer is reset until the next exit by the patient. If the deformation sensors 600 do not detect that the patient re-enters the bed 100 within the predetermined duration, a prolonged exit alarm is activated.

In one embodiment, the location determination unit 800 can further be configured to determine if a patient moves sufficiently while positioned on the bed 100. More specifically, the location determination unit 800 may be adapted to monitor the displacement of the patient on the bed 100 over an extended period of time. A bedsore alarm may be triggered if the patient does not move by at least a predetermined amount over a predetermined period. It will be appreciated that this may help to prevent the patient from developing bed sores.

In one embodiment, the bed exit alarm, the displacement speed alarm, the prolonged exit alarm described above include one or more notifications that can appear or be emitted on a medical staff interface which is located on the bed 100, near the bed 100 and/or at a remote staff location. In an example embodiment, the notifications appear on a screen which is located near the bed 100 and a visual and auditory alarm is further emitted at a medical staff interface located away from the bed 100, where medical staff on duty are likely to notice the alarms. Communication with the medical staff interface can be made via a wired or wireless connection.

Furthermore, information about the patient can also be displayed on the same interface to help the medical staff in identifying which alarms would be appropriate for the patient in care. The visual notifications can be presented as icons, for example a "Fall Risk" icon can be displayed on the user interface to warn the medical staff that this patient may fall off the bed 100 during an unsupervised exit. These icons can be presented continuously or as a screen saver display, with movement or blinking features.

In the illustrated embodiment, the deformation sensors 600 may also be used to determine a longitudinal location of the patient on the bed 100. As explained above, the deformation sensor assemblies 350, 352 are located about halfway between the upper leg end 342a of the head elevation assembly 320 and the upper leg end 342b of the foot elevation assembly 330, which is the location where the largest deformations may be sensed. Furthermore, this is also the longitudinal location on the frame 200 where a load applied on the frame 200 will cause the biggest deformation or deflection in the longitudinal frame members. As the load is moved towards the upper leg end 342a of the head elevation assembly 320 or towards the upper leg end 342b of the foot elevation assembly 330, the deformation sensed in the longitudinal frame members 300, 302 will decrease. Therefore, as the patient moves towards the head end 102 or the foot end 104 of the bed 100, the load application point will move as well towards the head end 102 or foot end 104 of the bed 100, causing the longitudinal frame members 300, 302 to undergo less deflection. This in turn causes the sum of the voltage value VG and the voltage value VR to decrease just as if weight was removed from the frame 200.

In the illustrated embodiment, the upper leg end 342a of the head elevation assembly 320 and the upper leg end 342b of the foot elevation assembly 320 are spaced from each other by a longitudinal distance L. In the illustrated embodiment, the longitudinal distance L is shorter than the longitudinal frame members 300, 302. More specifically, the longitudinal frame members 300, 302 extends longitudinally beyond the upper leg end 342a of the head elevation assembly 320 towards the head end 102 of the bed 100 and beyond the upper leg end 342b of the foot elevation assembly 330 towards the foot end 104 of the bed 100, as best shown in FIGS. 3 to 5.

In one embodiment, the longitudinal distance L is about 68 inches or 172.7 cm, and the length of the longitudinal frame members 300, 302 is about 80 inches or 203.2 cm. Alternatively, the longitudinal distance L and the length of the longitudinal frame members 300, 302 could be different.

In the illustrated configuration, a load applied beyond the upper leg end 342a of the head elevation assembly 320 or beyond the upper leg end 342b of the foot elevation assembly 330 generates substantially very little deformation or deflection in the center of the frame 200. It will therefore be understood that accessories such as IV bags, pumps, panels, linen can be added or removed from the head end 102 or foot end 104 of the bed 100 without their mass significantly altering the determination of the longitudinal location of the patient.

In one embodiment, an initial voltage value VGA and an initial voltage value VRA are first measured. These initial voltage values VGA and VRA may be measured when the patient is lying on the bed 100 in a normal resting position.

The longitudinal location of the load application point can be calculated using the following formula:

$$Pos(y) = \frac{L}{2} * \left( \frac{VG + VR}{VGA + VRA} \right) \quad (4)$$

in which L is the distance between the upper leg end 342a of the head elevation assembly 320 and the upper leg end 342b of the foot elevation assembly 330, VG is the voltage value of the deformation sensor 600 of the left deformation sensor assembly 350, VR is the voltage value of the deformation sensor 600 of the right deformation sensor assembly 352, VGA is the initial voltage value of the deformation sensor 600 of the left deformation sensor assembly 350 and VRA is the initial voltage value of the deformation sensor 600 of the right deformation sensor assembly 352.

It will be understood from the formula (4) above that a displacement of the load application point from a transversal centerline $C_{LT}$ of the frame 200 towards one of the head end 102 and the foot end 104 causes a decrease in voltage in both deformation sensors 600. It will be appreciated that this decrease is a scalar value and therefore does not provide an indication of a longitudinal direction in which the load application point is displaced.

It will also be understood that the longitudinal location Pos(y) in which measurements of the initial voltage values VGA, VRA is L/2, and that the longitudinal location Pos(y) of the upper leg end 342a of the head elevation assembly 320 and the upper leg end 342b of the foot elevation assembly 330, where no deformation is measured by the deformation sensors 600, is 0. In one embodiment in which the longitudinal distance L is about 68 inches or 172.7 cm, the longitudinal location Pos(y) which corresponds to L/2 is 34 inches or 86.4 cm.

In one example, the initial voltage values VGA, VRA are measured when the load application point is at the transversal centerline $C_{LT}$ between the upper leg end 342a of the head elevation assembly 320 and the upper leg end 342b of the foot elevation assembly 330. If the load application point is not at this longitudinal center when the initial voltage values VGA, VRA are measured, the location at which the initial voltage values VGA, VRA are measured is still considered to be L/2 and the calculated distances may be scaled accordingly. For example, if the initial voltage values VGA, VRA are measured when the load application point is located at 10 inches or 25.4 cm from the upper leg end 342a of the head elevation assembly 320, the location determination unit 800 will consider that this longitudinal location Pos(y) corresponds to L/2, in accordance with formula (4). Therefore, if a value of L of 68 inches or 172.7 cm was inputted in the location determination unit 800, the location determination unit 800 will consider that the initial longitudinal location Pos(y), which is in reality at 10 inches or 25.4 cm, is at 34 inches or 86.4 cm. Furthermore, the location determination unit 800 will still consider the longitudinal location Pos(y) of the top end of the head elevation assembly to be 0. Therefore, the location determination unit 800 may, in this case, consider a distance of 10 inches or 25.4 cm to be in fact a distance of 34 inches or 86.4 cm.

In some circumstances, it may be desirable to reduce or eliminate this scaling. For this purpose, the value of L/2 may be re-determined periodically in a closed-loop fashion such that the value of L/2 used to determine the longitudinal location Pos(y) of the patient will be substantially close to the real value of L/2 (i.e. half the distance L between the upper leg end 342a of the head elevation assembly 320 and the upper leg end 342b of the foot elevation assembly 330). It will be understood that if the initial voltage values VGA, VRA are measured when the load application point is not centered on the bed 100 and the load application point is subsequently displaced towards the transversal centerline $C_{LT}$ of the bed 100, the longitudinal location Pos(y) will be larger than L/2. In one embodiment, the location determination unit 800 is configured for periodically measuring the longitudinal location Pos(y) and comparing it with the currently stored value of L/2. If the measured longitudinal location Pos(y) is larger than the currently stored value of L/2, the location determination unit 800 determines that the current longitudinal location Pos(y) of the load application point is closer to the longitudinal center of the bed 100 and the measured longitudinal location Pos(y) becomes the new L/2. In this configuration, the stored value of L/2 therefore converges towards the real value of L/2.

In one embodiment, the determination of the longitudinal location of the patient is used to activate the bed exit alarm to activate the alarm when the patient exits the bed 100 from the upper end 102 or foot end 104 of the bed 100. The location determination unit 800 first determines a longitudinal location of the patient on the bed 100. More specifically, the location determination unit 800 determines the longitudinal location Pos(y) using formula (4) above. If the longitudinal location Pos(y) is lower than 0, then the bed exit alarm is activated. In this configuration, the bed exit alarm is activated when the load application point is displaced beyond the upper leg end 342a of the head elevation assembly 320 towards the head end 102 of the bed 100 or beyond the upper leg end 342b of the foot end elevation assembly 330 towards the foot end 104 of the bed 100, which corresponds to the patient exiting the bed 100.

In another configuration, the minimum threshold value is 4 inches or 10.2 cm. In this configuration, the bed exit alarm is activated when the load application point is displaced within 4 inches or 10.2 cm of the upper leg end 342a of the head elevation assembly 320 or of the upper leg end 342b of the foot elevation assembly 330, which corresponds to the patient most likely having the intention of exiting the bed 100.

In yet another configuration, the minimum threshold value is ((L/2)−1 inch) or ((L/2)−2.5 cm). In an embodiment in which the distance L between the upper leg end 342a of the head elevation assembly 320 and the upper leg end 342b of the foot elevation assembly 330 is 68 inches or 172.7 cm, the minimum threshold value is therefore 33 inches or 83.8 cm. In this configuration, the bed exit alarm is activated when the load application point is displaced within 1 inch or 2.5 cm from the transversal centerline $C_{LT}$ of the bed 100, which corresponds to the patient having just woken up and stiffing in the bed 100.

In one embodiment, the location determination unit 800 is further operatively connected to one or more actuators of the bed 100 to control the actuators in relation to the transversal and/or longitudinal location of the patient in the bed 100. For example, the bed 100 may comprise a backrest actuator adapted to pivot the backrest 252 relative to the frame 200, and a lower body actuator for pivoting the lower body support panel 254 and the core support panel 258 adjacent the lower body support panel 254. The location determination unit 800 may be configured to stop actuation of these actuators if a determination that the patient is exiting the bed 100 is made. Alternatively, the processing unit may be configured to stop actuation of these actuators if a determination that the patient is at a predetermined location on the bed 100, such as a certain distance from the edge of the bed 100. By stopping actuation of the actuators before the patient exits the bed, injuries to the patient may be prevented.

In one embodiment, the bed 100 may further comprise a plurality of wheels 150 (shown in FIG. 1) and an electrical brake system (not shown) operatively coupled to the wheels 150. The electrical brake system could be operatively connected to the location determination unit 800 and be configured to immobilize the bed 100 by activating the electrical brake system when the weight of the patient shifts on the bed 100. For example, if a patient tries to enter the bed 100 and leans on the bed 100 to climb in, the weight displacement assembly would notice a sudden weight on one side of the bed 100 and could trigger the electrical brake system.

Figure 14:
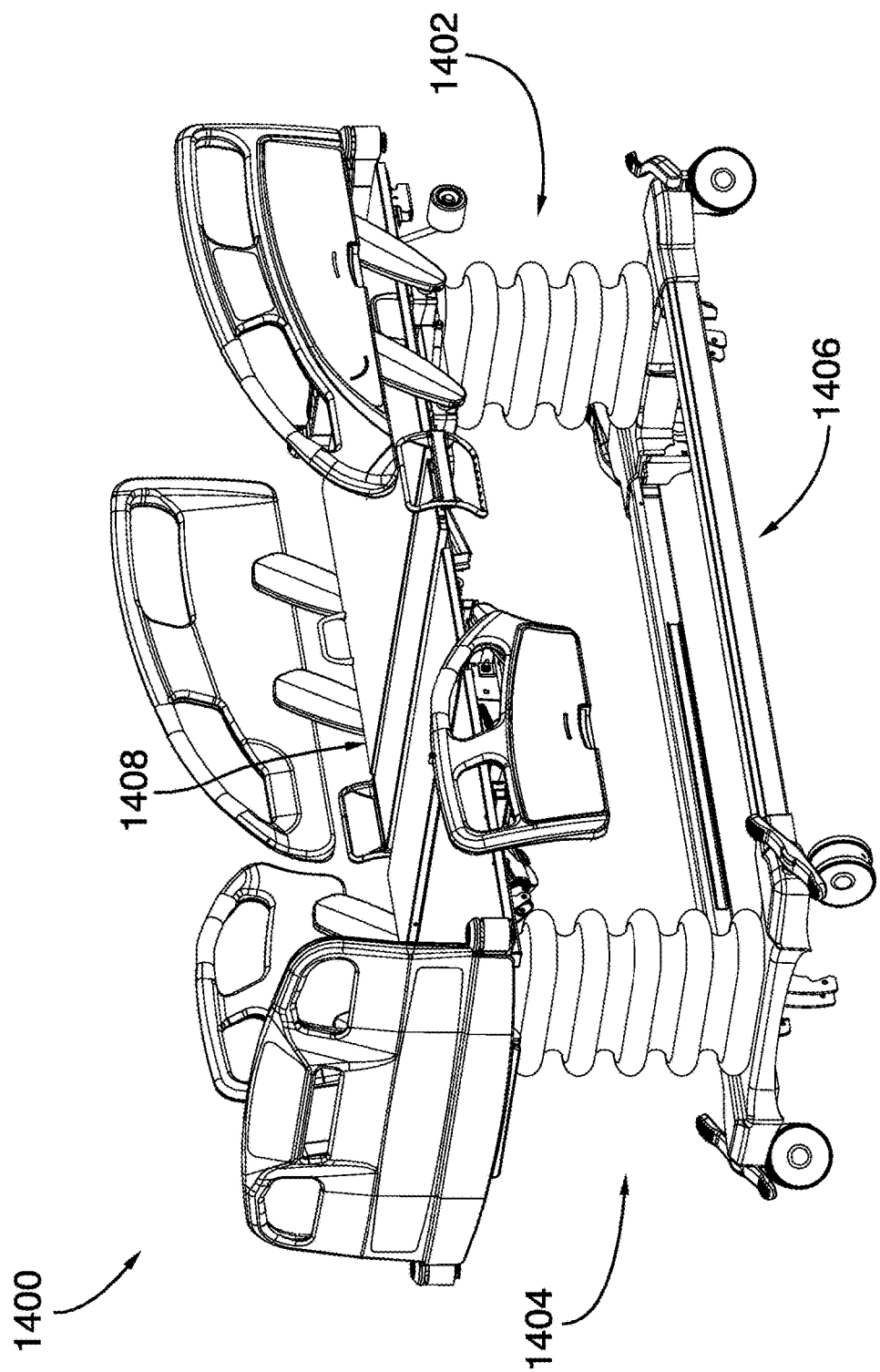
FIG. 14 is a top perspective view of a hospital bed, in accordance with an alternative embodiment.
Figure 15:
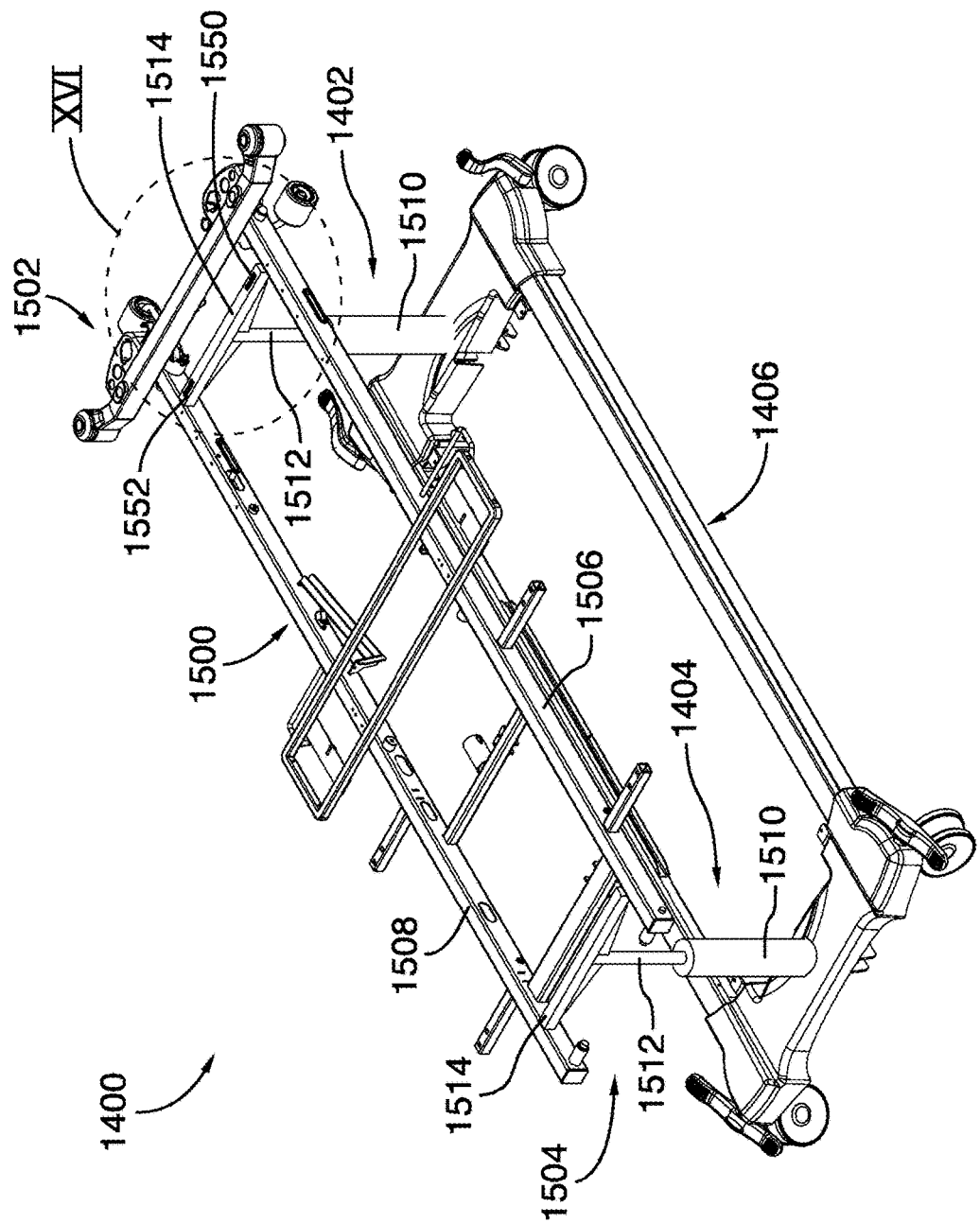
FIG. 15 is a top perspective view of the hospital bed shown in FIG. 14, with the patient support surface, railings and bellows removed.
Figure 16:
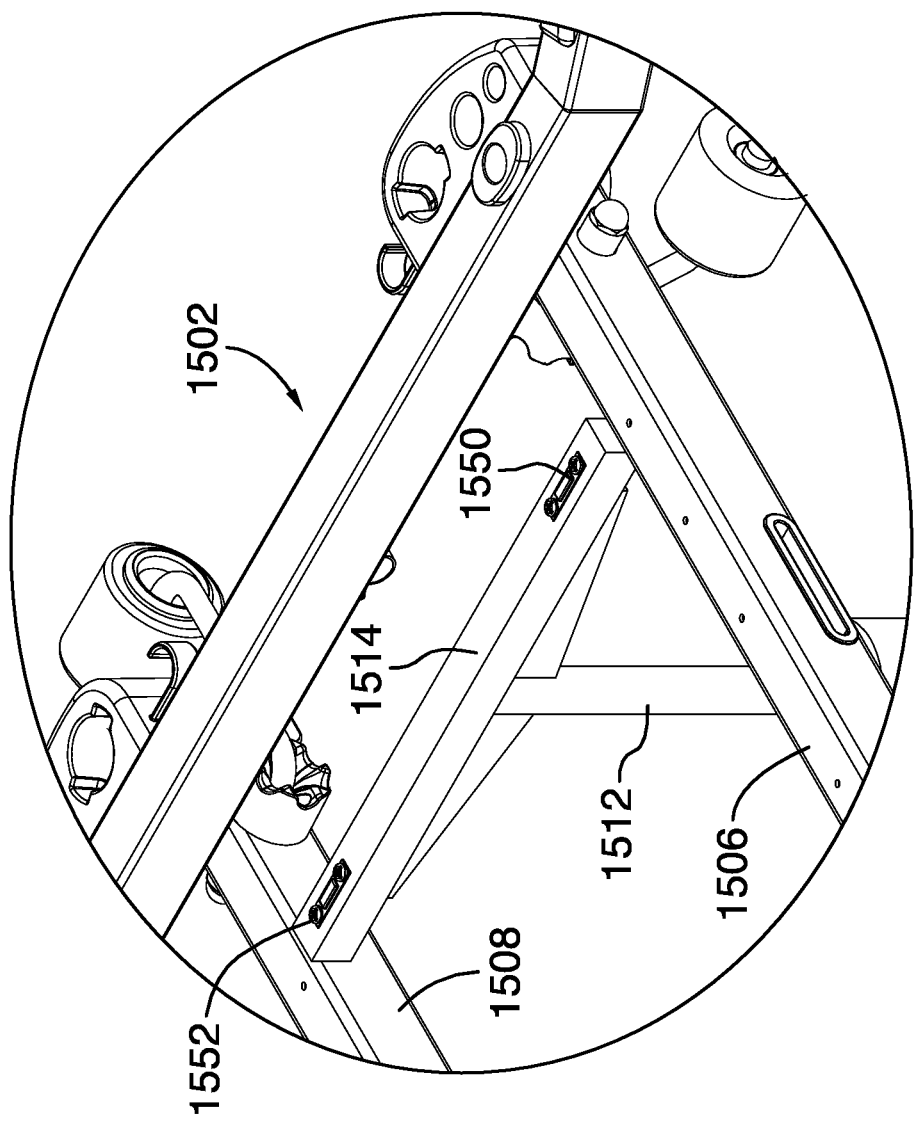
FIG. 16 is a partial top perspective view of the hospital bed shown in FIG. 15 taken from the encircled area XVI.

Now referring to FIGS. 14 to 16, there is shown a hospital bed 1400 in accordance with an alternative embodiment. In this embodiment, the head and foot elevation assemblies are replaced by head and foot hydraulic jacks 1402, 1404 which can be raised and lowered to selectively raise, lower and tilt the bed 1400. The bed 1400 comprises a base 1406 and a patient support assembly 1408 connected to the base 1406 via the hydraulic jacks 1402, 1404.

As best shown in FIG. 15, the patient support assembly 1408 comprises a frame 1500 generally similar to the frame of the bed shown in FIGS. 1 to 6B. More specifically, the frame 1500 comprises a head end 1502, a foot end 1504, a left longitudinal frame member 1506 and a right longitudinal frame member 1508. Each hydraulic jack 1402, 1404 comprises a cylinder 1510 which extends generally vertically from the base 1406, a piston rod 1512 and a cross-member 1514 secured on the piston rod 1512 such that the piston rod 1512 and the cross-member 1514 define a T-shaped configuration. The cross-member 1514 of the head hydraulic jack 1402 extends between and connects together the left and right longitudinal frame members 1506, 1508 near the head end 1502 of the frame 1500. Similarly, the cross-member 1514 of the foot hydraulic jack 1404 extends between and connects together the left and right longitudinal frame members 1506, 1508 near the foot end 1504 of the frame 1500.

In the illustrated embodiment, the bed 1400 further comprises a left deformation sensor 1550 and a right deformation sensor 1552. The left deformation sensor 1550 is secured on the cross-member 1514 of the head hydraulic jack 1402 near the left longitudinal member 1506 and the right deformation sensor 1552 is secured on the cross-member 1514 of the head hydraulic jack 1402 near the right longitudinal member 1508. Each deformation sensor 1550, 1552 is generally disposed parallel to the longitudinal axis of the cross-member 1514, and is therefore disposed transversely relative to the frame 1500. The left and right deformation sensors 1550, 1552 are generally similar to the deformation sensors 600 illustrated in FIGS. 6 to 7 and described above. In this configuration, the deformation sensors 1550, 1552 are adapted for measuring deformations in the cross-member 1514, which could be caused by a load being applied on the cross-member 1514 directly or on the left and right longitudinal frame members 1506, 1508 connected to the cross-member 1514. In one embodiment, the deformation sensors 1550, 1552 are adapted to determine the transversal location Pos(x) using substantially the same method described above. Similarly, the deformation sensors 1550, 1552 could be adapted to determine the longitudinal location Pos(y) also using substantially the same method described above. Alternatively, the deformation sensors 1550, 1552 could be adapted to determine the transversal location Pos(x) and/or the longitudinal location Pos(y) of the load application point using any other method deemed by the skilled addressee to be suitable.

In the embodiments described above, the bed 100 comprises a left deformation sensor assembly and a right deformation sensor assembly. In an alternative embodiment, the bed 100 could instead comprise a single deformation sensor configured for determining the transversal location Pos(x) of the load application point using the torsion caused by the load application point being located at a distance from the longitudinal centerline of the frame.

Figure 17:
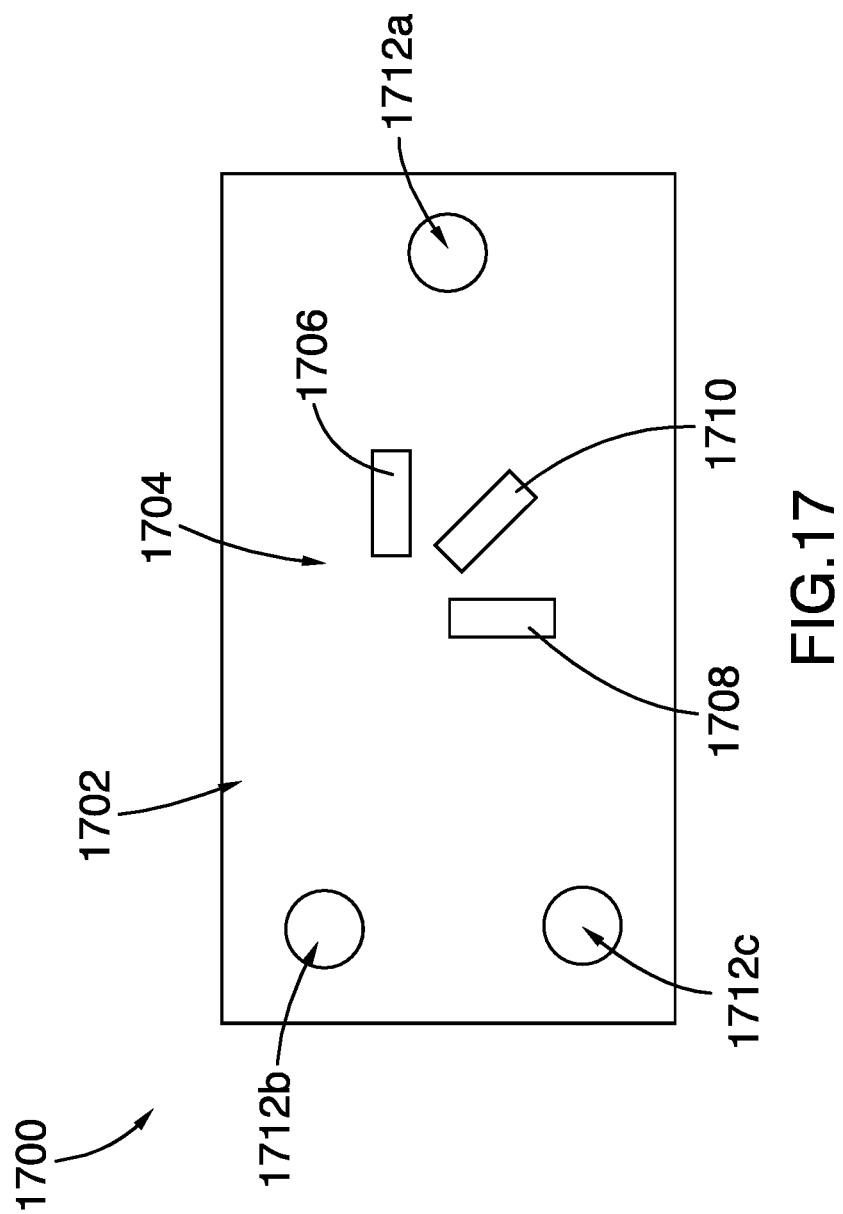
FIG. 17 is a schematic drawing of a deformation sensor in accordance with an alternative embodiment.

Referring to FIG. 17, there is shown a deformation sensor 1700 which comprises a mounting plate 1702 adapted to be secured to a planar surface of one of the left and right longitudinal frame members 300, 302 and a strain gauge rosette 1704 mounted on the mounting plate 1702. The strain gauge rosette 1704 comprises a first strain gauge 1706 adapted to be disposed parallel to the longitudinal frame member 300, 302, a second strain gauge 1708 disposed perpendicular to the first strain gauge 1706 and a third strain gauge 1710 disposed at a 45 degree angle between the first and second strain gauges 1706, 1708. In this embodiment, the mounting plate 1702 comprises three mounting holes 1712*a*, 1712*b* 1712*c* disposed in a triangular configuration and adapted to receive fasteners (now shown) to secure the mounting plate 1702 on the upper surface 650 of the longitudinal frame member 300, 302 such that the mounting plate 1702 is deformed similarly to the upper surface 650 of the longitudinal frame member 300, 302 both in bending and in torsion. This configuration allows the deformation sensor 1700 to measure deformation in the longitudinal frame member 300, 302 both in bending and in torsion. It will be appreciated that this would allow a single deformation sensor to be used instead of two.

To determine the longitudinal position Pos(y) of the load application point, the same method described above can be used, but applied to only a single deformation sensor. Specifically, the following formula, simplified from formula (4), can be used:

$$Pos(y) = \frac{L}{2} * \left(\frac{V}{VA}\right) \quad (5)$$

in which L is the distance between the upper leg end 342*a* of the head elevation assembly 320 and the upper leg end 342*b* of the foot elevation assembly 330, V is the voltage value of the deformation sensor 1700 and VA is the initial voltage value of the deformation sensor 1700.

To determine the transversal position Pos(x) of the load application point, the voltage value from the torsion measured by the strain gauge rosette 1704, or torsion voltage value, is used. In one embodiment, the torsion voltage value varies proportionally to the distance from the longitudinal centerline of the frame 200. It would therefore be possible to determine the transversal location Pos(x) as a function of the torsion voltage value using techniques similar to the techniques described above. Alternatively, the torsion voltage value may not vary proportionally to the distance from the longitudinal centerline of the frame 200. In this case, other techniques know to the skilled addressee may be used to determine the transversal location Pos(x) of the load application point.

Figure 18:
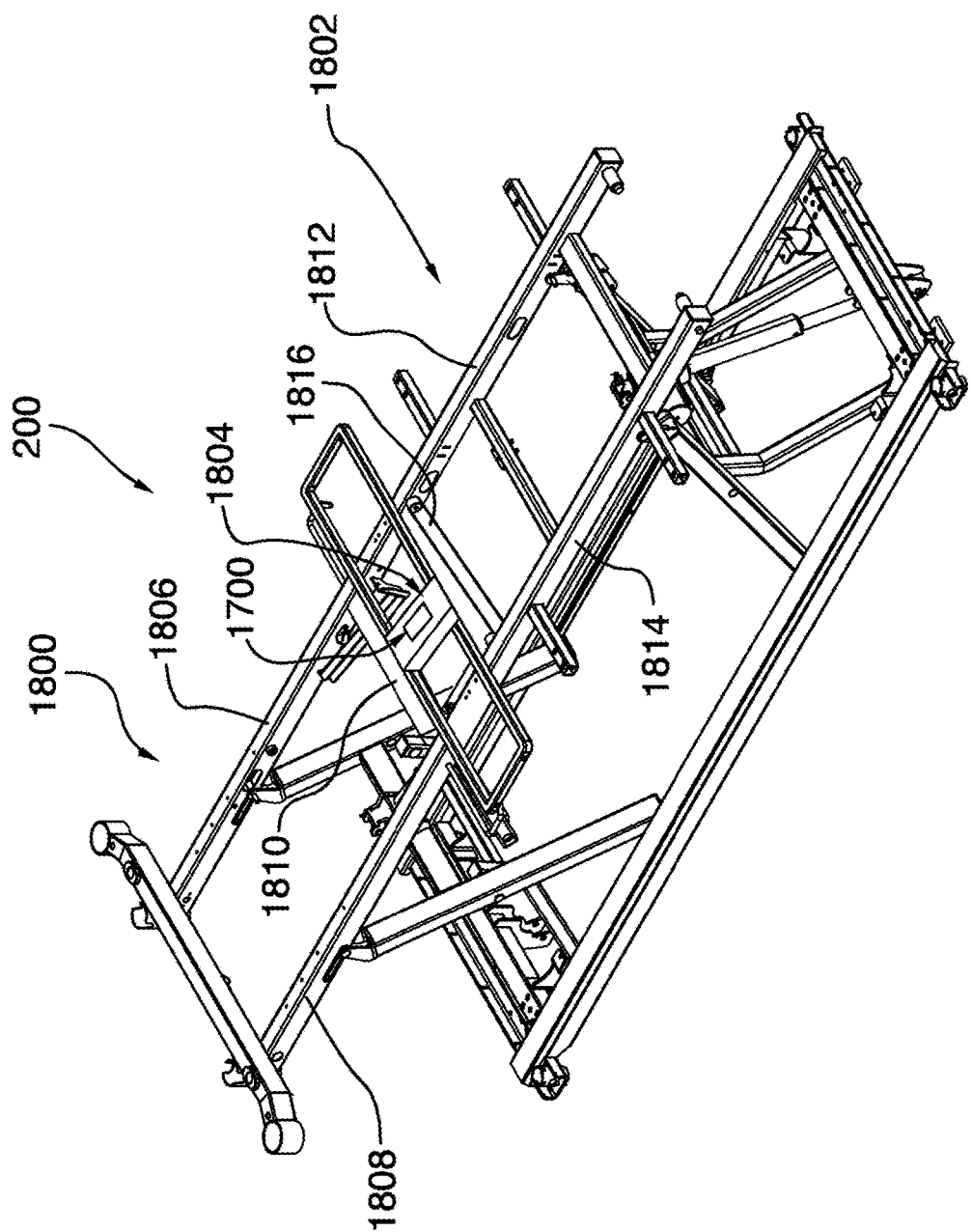
FIG. 18 is a top perspective view of a frame for a hospital bed, in accordance with another alternative embodiment, with the frame mounted on an elevation assembly and a base.

Turning to FIG. 18, the frame 200 may be configured specifically to allow the deformation sensor to be placed in an area where deformation is maximal and even amplified, which provides a substantially more accurate determination of the transversal location Pos(x) of the load application point. Specifically, the frame 200 could comprise a head subframe 1800 located near the head end 102 of the bed 100 and a foot subframe 1802 located near the foot end 104 of the bed 100, the head and foot subframes 1800, 1802 being connected together by a central longitudinal frame member 1804 disposed along the centerline of the frame 200. In the illustrated embodiment, the head subframe 1800 comprises a left longitudinal member 1806, a right longitudinal member 1808 and an end transverse member 1810 extending transversally between the left and right longitudinal members 1806, 1808. Similarly, the foot subframe 1802 comprises a left longitudinal member 1812, a right longitudinal member 1814 and an end transverse member 1816 extending transversally between the left and right longitudinal members 1812, 1814. The end transverse member 1816 of the foot subframe 1802 is located towards the head subframe 1800 and the end traverse member 1810 of the head subframe 1800 is located towards the foot subframe 1802. The end transverse members 1810, 1816 are generally parallel to each other and are connected together by the central longitudinal frame member 1804 which extends generally perpendicular to the end transverse members 1810, 1816. In the illustrated embodiment, the central longitudinal frame member 1804 has a generally rectangular cross-section and the deformation sensor 1700 is secured to an upper planar surface of the central longitudinal frame member 1804.

When assembled together, the head subframe 1800, the foot subframe 1802 and the central longitudinal frame member 1804 have about the same dimensions as the frame of the embodiment shown in FIGS. 1 to 6B, and are adapted to support a patient support assembly similar to the patient support assembly 108 shown in FIG. 1. However, the configuration of the frame 200 illustrated in FIG. 18 makes it more flexible in torsion than the frame 200 of the bed 100 shown in FIGS. 1 to 6B because a single beam-like member with a rectangular cross-section such as the central longitudinal frame member has less resistance to torsion than the two spaced-apart longitudinal frame members of the frame illustrated in FIGS. 1 to 6B, as a skilled person will appreciate. Since the frame provides larger deformations in torsion at the central longitudinal frame member, it also allows more accurate measurements to be taken by the deformation sensor.

Figure 10:
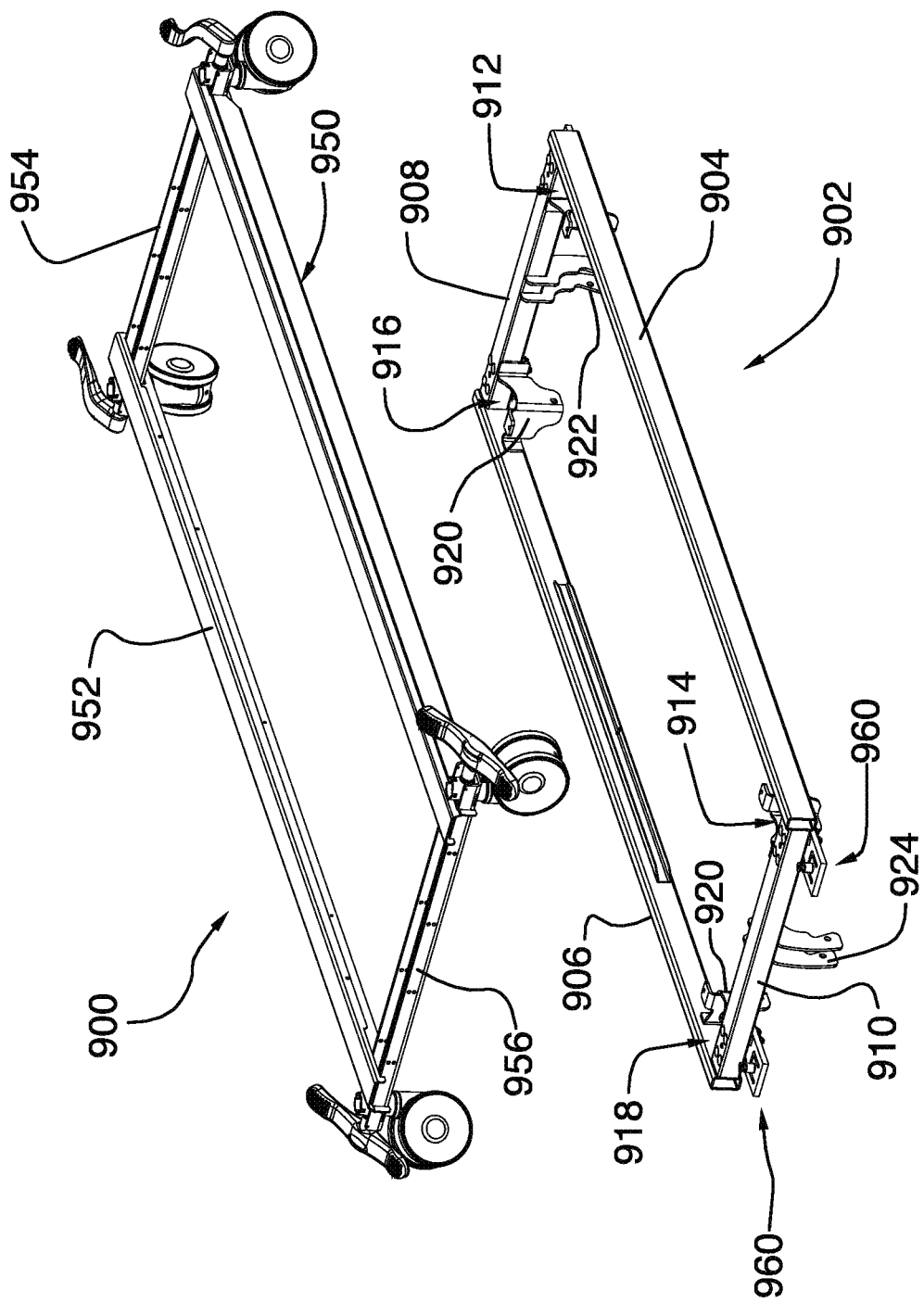
FIG. 10 is an exploded top perspective view of the base shown in FIG. 9, with the suspended frame exploded away from the fixed frame.

Now turning back to FIG. 10, the bed 100 further comprises a weight measurement system for measuring the weight of the patient lying on the bed 100. It will be appreciated that this system is distinct from the deformation sensors 600 described above. The deformation sensors 600 may not provide a weight measurement with a sufficient precision. In such a case where a relatively higher degree of precision is desired, the weight measurement system can be provided on the bed 100. Specifically, the weight measurement system is provided in the base 106 of the bed 100.

In the illustrated embodiment, the base 106 is generally rectangular and comprises a fixed frame 900 and a suspended frame 902 movably connected to the fixed frame 900. The suspended frame 902 comprises parallel left and right longitudinal members 904, 906 and parallel head and foot transversal members 908, 910 which extend between and connect the left and right longitudinal members 904, 906 at the head and foot ends 102, 104 of the bed 100, respectively. More specifically, the left longitudinal member 904 is connected to the head transversal member 908 at a left head corner 912 of the suspended frame 902 and to the foot transversal member 910 at a left foot corner 914 of the suspended frame 902. Similarly, the right longitudinal member 906 is connected to the head transversal member 908 at a right head corner 916 of the suspended frame 902 and to the foot transversal member 910 at a right foot corner 918 of the suspended frame 902.

In the illustrated embodiment, each one of the left and right longitudinal members 904, 906 and each one of the head and foot transversal members 908, 910 is hollow and has a generally rectangular cross-section. It will be appreciated that this configuration provides the suspended frame 902 with relatively good resistance to bending and torsion while allowing the suspended frame 902 to have a relatively low weight.

The suspended frame 902 further includes corner braces 920 connecting adjacent transversal and longitudinal members. The corner braces brace the suspended frame by maintaining the transversal members perpendicular to the longitudinal members, and are also adapted to be pivotably connected to the lower ends 500 of the pivoting links 346. The suspended frame 902 further comprises head and foot actuator brackets 922, 924 extending downwardly from the head and foot transversal members, respectively. The head actuator bracket 922 is adapted to be pivotably connected to the elevation actuator 334 of the head elevation assembly 320 and the foot actuator bracket 924 is adapted to be pivotably connected to the elevation actuator 334 of the foot elevation assembly 320. Still in the illustrated embodiment, the suspended frame 902 further comprises a pair of longitudinal tracks secured to the left and right longitudinal members 904, 906. The longitudinal tracks are adapted to slidably receive the lower end 344 of the pivoting leg members 332 of the elevation assembly 110.

In this configuration, the entire elevation assembly 110 is therefore connected to the suspended frame 902 via the elevation actuators 334, the pivoting leg members 332 and the pivoting links 346 of the elevation assembly 110. More specifically, the elevation assembly 110 is only connected to the fixed frame 900 indirectly via the suspended frame 902, as will be explained further below.

Figure 9:
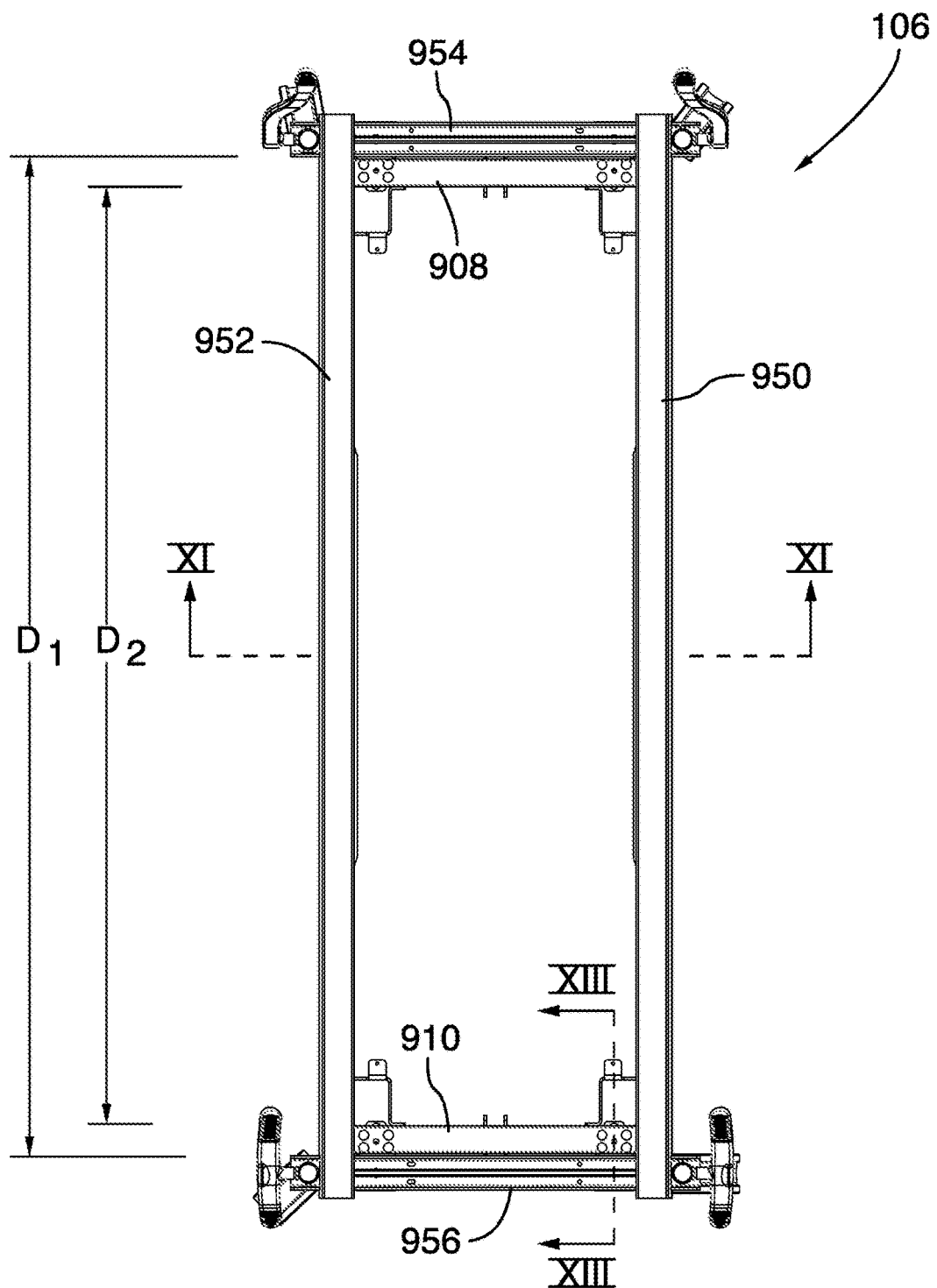
FIG. 9 is a top plan view of the base for the bed shown in FIG. 1.

Still referring to FIG. 9, the fixed frame 900 comprises parallel left and right longitudinal members 950, 952 and parallel head and foot transversal members 954, 956 which extend between and connect the left and right longitudinal members 950, 952 at the head and foot ends 102, 104 of the bed 100, respectively.

Figure 11:
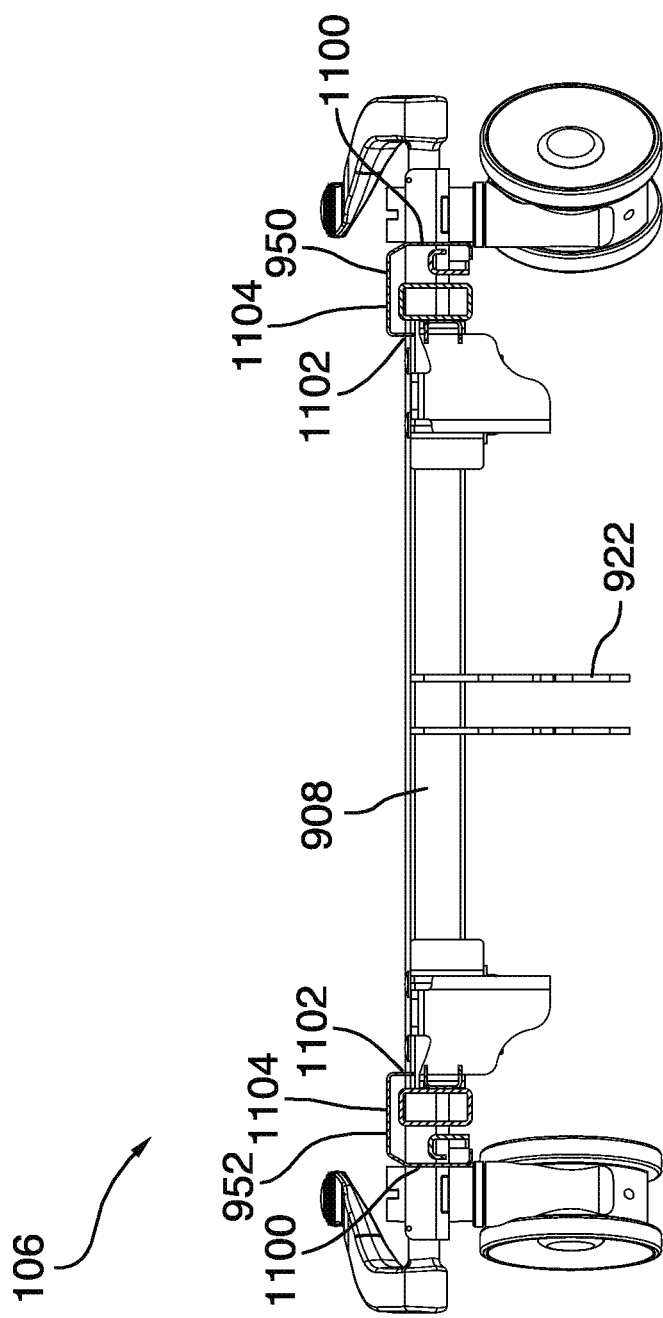
FIG. 11 is a cross-sectional view of the base shown in FIG. 9, taken along cross-section line XI-XI.

Turning to FIG. 11, the longitudinal members 950, 952 have a generally inverted J-shaped cross-section and include vertical outer and inner sidewalls 1100, 1102 and a top wall 1104 extending horizontally between the outer and inner walls 1100, 1102. The distance between the left and right longitudinal members 904, 906 of the suspended frame and the left and right longitudinal members 950, 952 of the fixed frame 900 are selected such that the left and right longitudinal members 904, 906 of the suspended frame 902 are respectively received within the left and right longitudinal members 950, 952 of the fixed frame 900. The fixed frame 900 and the suspended frame 902 therefore extend generally in a common horizontal plane P. This configuration allows the base 106 to be relatively compact.

Referring back to FIG. 10, the head and foot transversal members 954, 956 of the fixed frame 900 have a U-shaped cross-section and are spaced from each other by a distance $D_1$, while the head and foot transversal members 908, 910 of the suspended frame 902 are spaced from each other by a distance $D_2$ which is smaller than the distance $D_1$. This configuration allows the suspended frame 902 to fit within the fixed frame 900. Specifically, the distances $D_1$ and $D_2$ are selected such that the head transversal member 908 of the suspended frame 902 is adjacent the head transversal member 954 of the fixed frame 900, and that the foot transversal member 910 of the suspended frame 902 is adjacent the foot transversal member 956 of the fixed frame 900.

The base 106 further comprises a plurality of load sensors which are adapted to connect the suspended base 902 to the fixed base 900 while providing an indication of the weight on the bed 100. In the illustrated embodiment, the base 106 includes four load sensors 960, each disposed near one of the corners 912, 914, 916, 918 of the suspended frame 902.

Figure 12:
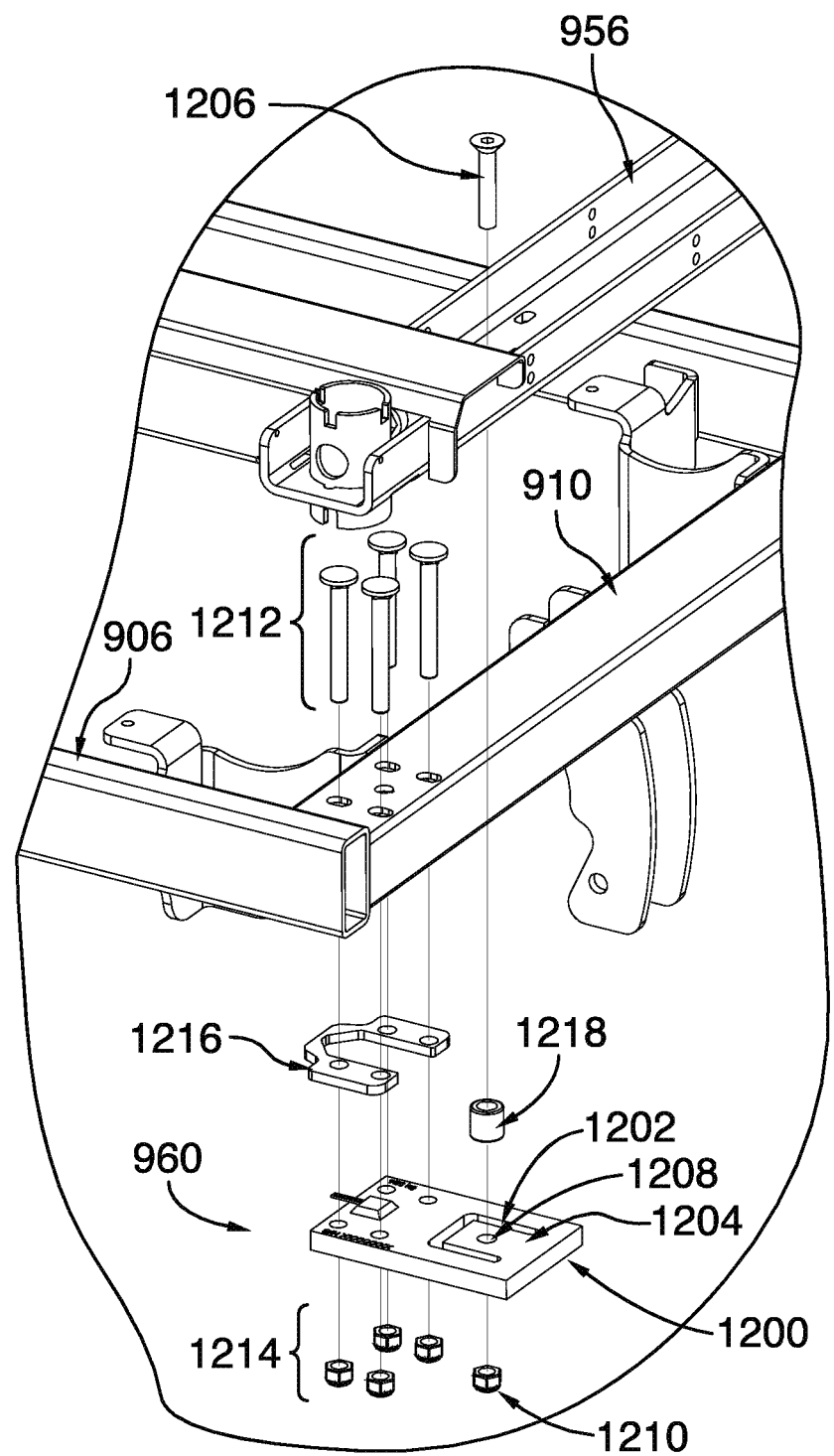
FIG. 12 is an exploded view of a load sensor for the base shown in FIG. 10, showing details of the connection of the suspended frame to the fixed frame via the load sensor.

Referring now to FIG. 12, each load sensor 960 comprises a connecting plate 1200 having a U-shaped slit 1202 which defines a cantilevered tongue portion 1204 and one or more strain gauges, not shown, operatively connected to the cantilevered tongue portion 1204. The connecting plate 1200 is fastened to the underside of one of the head and foot transversal elements 908, 910 of the suspended frame 902, and is cantilevered outwardly towards the corresponding transversal member 954, 956 of the fixed frame 900.

A suspension member or bolt 1206 is inserted through the transversal member 954, 956 of the fixed frame 900 and through an opening 1208 in the cantilevered tongue portion 1204, and is secured to the cantilevered tongue portion 1204 with a nut 1210.

It will be appreciated that to obtain precise weight measurements, it may be desirable to have very little movement of the connecting plate 1200 relative to the suspended frame 902. In the illustrated embodiment, the connecting plate 1200 is fastened to the suspended frame 902 with four bolts 1212 and corresponding nuts 1214. A spacer 1216 is further provided between the transversal member 910 of the suspended frame 902 and the connecting plate 1200 to space the connecting plate 1200 from the suspended frame 902. Alternatively, the connecting plate 1200 could be connected fastened to the suspended frame using a different number of bolts, or using another type of attachment known to the skilled addressee.

An annular spacer 1218 is also provided on the suspension bolt 1206, between the connecting plate 1200 and the transversal member 956 of the fixed frame 900, to reduce or eliminate play between the suspended frame 902 and the fixed frame 900. This is particularly useful when lifting the bed and during transportation or impact so as not to damage the load sensors 960.

Figure 13:
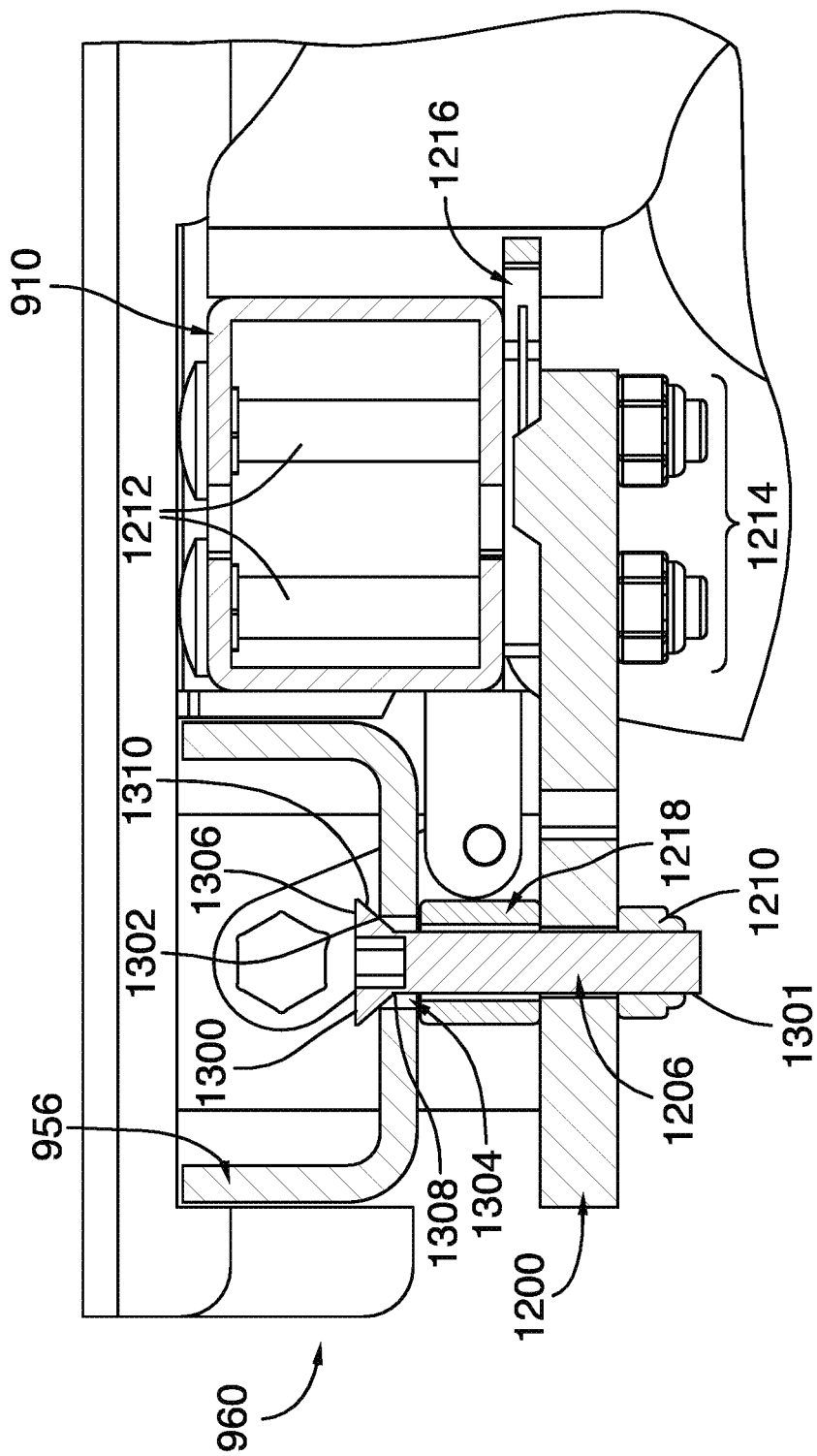
FIG. 13 is a cross-sectional view of the base shown in FIG. 9, taken along cross-section line XIII-XIII.

Referring to FIG. 13, the suspension bolt 1206 has a head 1300 and a bolt body 1301 which extends away from the head 1300. In the illustrated embodiment, the head 1300 is conical and is adapted to abut an edge 1302 of a hole 1304 in the transversal member 956 of the fixed frame 900.

Specifically, the head 1300 has an upper end 1306, a lower end 1308 and a lower surface 1310 extending between the upper and lower ends 1304, 1306 which tapers towards the bolt body 1301. In this configuration, the upper end 1304 has as first diameter and the lower end 1306 has a second diameter smaller than the first diameter. Still in the illustrated embodiment, the hole 1304 is circular and has a third diameter which is smaller than the first diameter but greater than the second diameter, such that the lower end 1306 of the head 1300 is located below the edge 1302 of the hole 1304 but the upper end 1304 of the head 1300 is located above the edge 1302. In this configuration, the suspension bolt 1206 therefore has only tangential contact with the fixed frame 900, thereby minimizing friction between the suspension bolt 1206 and the fixed frame 900 which may disturb the weight measurements. It will further be appreciated that the weight of the bed 100 pushes the head 1300 downwardly into tangential contact with the edge 1302 to therefore substantially eliminate all lateral movement of the suspended frame 902 relative to the fixed frame 900 without restraining the suspended frame 902 vertically. Alternatively, the suspension bolt 1206 may have a spherical or semi-spherical head, or a head having any other shape that has a lower surface that converges downwardly such that it would only tangentially contact the edge 1302 of the hole 1304.

It will be appreciated that in this configuration, the entire weight of the bed 100 rests on the suspension bolts 1206. Changes in weight on the bed 100 will cause changes in the deflection of the cantilevered tongue portion 1204 relative to the connecting plate 1200, resulting in a change in the impedance of the strain gauges. In one embodiment, a known input voltage is applied to the strain gauges and an output signal from the strain gauges varies as the resistance of the strain gauges vary to provide a signal indicative of the load applied to the load sensor 960. It will be appreciated, however, that other load sensors may alternatively be used, wherein such alternative load sensors include Linear Variable Displacement Transducers (LVDTs) and/or other weight detection devices operable in accordance with known capacitive, inductive, or other physical principles. All such alternative weight detection devices are contemplated herein. Example load cells which can be appropriately used by the person skilled in the art include co-planar beam load cell model 380 manufactured by Vishay Precision Group Inc. (Malvern, U.S.A.) and type PB planar beam load cell manufactured by Flintec Inc. (Hudson, U.S.A.).

It will be appreciated that the loads sensors 960 are provided in the base 106, where they are relatively protected. Furthermore, even if the support panels 252, 254, 256, 258 of the patient support surface 250 are partially angled, a compensation in the calculations to estimate the weight will not be necessary.

Alternatively, the load sensor 960 may not comprise connecting plates and suspension bolts. The suspended frame 902 may instead be suspended from the fixed frame 900 via tie-rods, chains, cables, grommet or other suspension devices considered suitable by the skilled addressee.

In another embodiment, this weight measuring system can be retrofitted to any known hospital bed or equipment by a service person. Such equipment can be a wheel chair, lifting and transfer equipment, etc. Calibration can be done on site by qualified personal.

A hospital bed is used to illustrate the examples described herein. However, other patient support devices, such as stretchers, adjustable chairs, home-care beds, etc., are also suitable for use with the described systems. Moreover, the term "patient" is not intended to be limiting, and can be taken to apply to any user of the support device, such as an individual undergoing short-term, medium-term or long-term care, a hospital patient, a nursing home resident, etc.

The embodiments described above are intended to be exemplary only. The scope of the invention is therefore intended to be limited solely by the appended claims.

We claim:

1. A weight sensing system for a hospital bed, the hospital bed having a base including a fixed frame adapted to be placed on a ground surface and a suspended frame supporting a patient support assembly, the system comprising:
    at least one load sensor adapted to be secured to the suspended frame;
    at least one suspension member configured to extend between the suspended frame and one of the at least one load sensor for vertically suspending the suspended frame from the fixed frame, each suspension member having a lower end secured to one of the at least one load sensor and an upper end abutting the fixed frame, the suspension member being unsecured from the fixed frame to allow free vertical movement of the suspended frame relative to the fixed frame,
    wherein each suspension member comprises a body located at the lower end of the suspension member for engaging the load sensor and a head located at the upper end of the suspension member abutting the fixed frame and wherein the suspension member is inserted in a hole of the fixed frame, the hole having a first diameter and the head of the suspension member having a second diameter larger than the first diameter to maintain the head above the fixed frame; and
    wherein each load sensor comprises a connecting plate having a U-shaped slit which defines a cantilevered tongue portion and at least one strain gauge operatively connected to the cantilevered tongue portion.

2. The system as claimed in claim 1, wherein the head of the suspension member is tapered towards the body of the suspension member and abuts an edge of the hole.

3. The system as claimed in claim 2, wherein the head of the suspension member has an upper end having the second diameter and a lower end having a third diameter smaller than the first and second diameters to allow the lower end of the head to extend below the edge of the hole.

4. The system as claimed in claim 2, wherein the head of the suspension member is conical.

5. The system as claimed in claim 1, wherein the connecting plate is fastened to the underside of one of the head and foot transversal elements of the suspended frame, and is cantilevered outwardly towards the corresponding transversal member of the fixed frame.

6. The system as claimed in claim 5, wherein the suspension member extends through the transversal member of the fixed frame and through an opening in the cantilevered tongue portion.

7. The system as claimed in claim 6, wherein the suspension member is secured to the cantilevered tongue portion with a nut.

8. The system as claimed in claim 5, wherein the connecting plate is fastened to the suspended frame with four bolts and corresponding nuts.

9. The system as claimed in claim 5, further comprising a spacer disposed between the transversal member of the suspended frame and the connecting plate to space the connecting plate from the suspended frame.

10. The system as claimed in claim 5, further comprising an annular spacer disposed on the suspension bolt between the connecting plate and the transversal member of the fixed frame.

11. A weight sensing system for a hospital bed, the hospital bed having a base including a fixed frame adapted to be placed on a ground surface and a suspended frame supporting a patient support assembly, the system comprising:
- at least one load sensor adapted to be secured to the suspended frame;
- at least one suspension member configured to extend between the suspended frame and one of the at least one load sensor for vertically suspending the suspended frame from the fixed frame, each suspension member having a lower end secured to one of the at least one load sensor and an upper end abutting the fixed frame, the suspension member being unsecured from the fixed frame to allow free vertical movement of the suspended frame relative to the fixed frame,
- wherein each load sensor comprises a connecting plate having a U-shaped slit which defines a cantilevered tongue portion and at least one strain gauge operatively connected to the cantilevered tongue portion.

12. The system as claimed in claim 11, wherein each suspension member comprises a body located at the lower end of the suspension member for engaging the load sensor and a head located at the upper end of the suspension member abutting the fixed frame.

13. The system as claimed in claim 11, wherein the suspension member is inserted in a hole of the fixed frame, the hole having a first diameter and the head of the suspension member having a second diameter larger than the first diameter to maintain the head above the fixed frame.

14. The system as claimed in claim 13, wherein the head of the suspension member is tapered towards the body of the suspension member and abuts an edge of the hole.

15. The system as claimed in claim 14, wherein the head of the suspension member has an upper end having the second diameter and a lower end having a third diameter smaller than the first and second diameters to allow the lower end of the head to extend below the edge of the hole.

16. The system as claimed in claim 14, wherein the head of the suspension member is conical.

17. The system as claimed in claim 11, wherein the connecting plate is fastened to the underside of one of the head and foot transversal elements of the suspended frame, and is cantilevered outwardly towards the corresponding transversal member of the fixed frame.

18. The system as claimed in claim 17, wherein the suspension member extends through the transversal member of the fixed frame and through an opening in the cantilevered tongue portion.

19. The system as claimed in claim 18, wherein the suspension member is secured to the cantilevered tongue portion with a nut.

20. The system as claimed in claim 17, wherein the connecting plate is fastened to the suspended frame with four bolts and corresponding nuts.

21. The system as claimed in claim 17, further comprising a spacer disposed between the transversal member of the suspended frame and the connecting plate to space the connecting plate from the suspended frame.

22. The system as claimed in claim 17, further comprising an annular spacer disposed on the suspension bolt between the connecting plate and the transversal member of the fixed frame.

* * * * *